(12) United States Patent
Wadman

(10) Patent No.: US 8,329,644 B2
(45) Date of Patent: Dec. 11, 2012

(54) LANTIBIOTIC-BASED COMPOUNDS HAVING ANTIMICROBIAL ACTIVITY

(75) Inventor: Sjoerd Nicolaas Wadman, Welwyn Garden City (GB)

(73) Assignee: Novacta Biosystems Limited, Hertfordshire (GB)

( * ) Notice: Subject to any disclaimer, the term of this patent is extended or adjusted under 35 U.S.C. 154(b) by 325 days.

(21) Appl. No.: 12/669,432

(22) PCT Filed: Jul. 18, 2008

(86) PCT No.: PCT/GB2008/002465
§ 371 (c)(1),
(2), (4) Date: Mar. 24, 2010

(87) PCT Pub. No.: WO2009/010765
PCT Pub. Date: Jan. 22, 2009

(65) Prior Publication Data
US 2010/0261638 A1    Oct. 14, 2010

(30) Foreign Application Priority Data
Jul. 18, 2007   (GB) .................................. 0714029.6

(51) Int. Cl.
*A61K 38/17* (2006.01)
(52) U.S. Cl. ..................................... 514/2.2
(58) Field of Classification Search ........................ None
See application file for complete search history.

(56) References Cited

U.S. PATENT DOCUMENTS

| | | | |
|---|---|---|---|
| 3,710,795 A | 1/1973 | Higuchi et al. | |
| 5,112,806 A | 5/1992 | Chatterjee et al. | |
| 5,304,540 A | 4/1994 | Blackburn et al. | |
| 5,667,991 A | 9/1997 | Koller et al. | |
| 5,683,675 A | 11/1997 | Vedia et al. | |
| 5,763,395 A | 6/1998 | Blackburn et al. | |
| 5,958,873 A | 9/1999 | Sakr et al. | |
| 5,985,823 A | 11/1999 | Goldstein | |
| 6,022,851 A | 2/2000 | Vertesy et al. | |
| 6,569,830 B1 | 5/2003 | Climo et al. | |
| 7,122,514 B2 | 10/2006 | Climo et al. | |
| 7,989,416 B2 * | 8/2011 | Boakes et al. ................. | 514/2.3 |
| 2009/0203583 A1 | 8/2009 | Wadman et al. | |
| 2010/0048459 A1 | 2/2010 | Boakes et al. | |
| 2010/0168410 A1 | 7/2010 | Cade et al. | |
| 2010/0179207 A1 | 7/2010 | Wadman | |

FOREIGN PATENT DOCUMENTS

| | | |
|---|---|---|
| DE | 197 45 583 | 4/1999 |
| EP | 0195359 | 9/1986 |
| EP | 0572942 | 12/1993 |
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |
| WO | WO 03/099862 | 12/2003 |
| WO | WO 2004/033706 | 4/2004 |
| WO | WO 2005/093069 | 10/2005 |
| WO | WO 2006/080920 | 8/2006 |
| WO | WO 2007/036706 | 4/2007 |

(Continued)

OTHER PUBLICATIONS

Boakes et al., "Organization of the biosynthetic genes encoding deoxyactagardine B (DAB), a new lantibiotic produced by *Actinoplanes liguariae* NCIMB41362," The Journal of Antibiotics, 63:351-358 (2010).

Han, "Advances in Characterization of Pharmaceutical Hydrates," Trends in Bio/Pharmaceutical Industry, 25-29 (Mar. 2006).

Vippagunta et al., "Crystalline solids," Adv. Drug Delivery Reviews, 48:3-26 (2001).

(Continued)

*Primary Examiner* — Thomas Heard
(74) *Attorney, Agent, or Firm* — Morgan, Lewis & Bockius LLP

(57) ABSTRACT

The present invention provides actagardine, actagradine B and deoxy actagardine B derivatives of formula (I), (I)

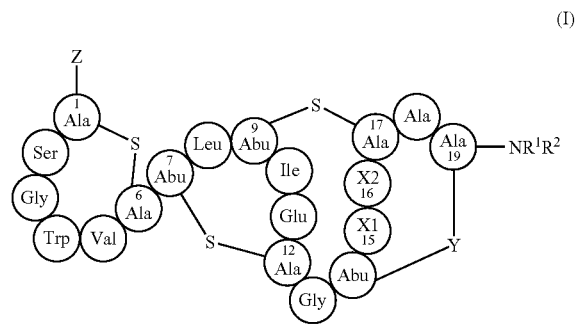

wherein: X1 denotes that the residue is Leu; Val; or Ile; X2 denotes that the residue is Leu; Val; or Ile; $R^1$ represents an alkyl or heteroalkyl group, substituted by at least one hydroxyl substituent, and $R^2$ represents hydrogen, or an alkyl or heteroalkyl group, optionally substituted by at least one hydroxyl substituent, or $R^1$ and $R^2$ taken together with the nitrogen atom represent a heterocyclic group having at least one hydroxyl substituent, wherein the heterocyclic group optionally further contains one or more heteroatoms; Z is an amino acid residue, $-NR^3R^4$, $-NR^5COR^6$, $-NR^5C(O)OR^6$; $-NR^5SOR^6$, $NR^5SO_2R^6$; $-NR^5C(S)NR^6R^7$, $-NR^5C(NR^8)NR^6R^7$, or $-N=R^9$, where $R^3$, $R^4$, $R^5$, $R^6$, $R^7$, $R^8$ and $R^9$ are independently hydrogen, or a group, optionally substituted, selected from alkyl, heteroalkyl, aryl, heteroaryl, aralkyl and heteroaralkyl, with the proviso that $R^9$ is not hydrogen; and Y is —S— or —S(O)—. The compounds find use in the treatment of microbial infections.

20 Claims, 5 Drawing Sheets

FOREIGN PATENT DOCUMENTS

| | | |
|---|---|---|
| WO | WO 2007/083112 | 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |
| WO | WO 2010/082019 | 7/2010 |
| WO | WO 2010/089544 | 8/2010 |

OTHER PUBLICATIONS

Examination Report in New Zealand Patent Application No. 569486 dated Mar. 10, 2011.
International Preliminary Report on Patentability in PCT/GB2010/000042 dated Apr. 19, 2011.
International Preliminary Report on Patentability in PCT/GB2010/000043 dated Apr. 14, 2011.
International Preliminary Report on Patentability in PCT/GB2010/000188 dated Apr. 19, 2011.
Non-final office action issued in U.S. Appl. No. 12/686,135 dated Apr. 28, 2011.
Office Action issued in European Patent Application No. 10000242.1 dated May 19, 2011.
Office Action issued in Chinese Application No. 200780006748.0 dated Mar. 23, 2011 (Translation included).
Notice of Allowance mailed in U.S. Appl. No. 12/161,221 dated May 12, 2011.
Altena et al. "Biosynthesis of the lantibiotic mersacidin: organization of a type B lantibiotic gene cluster" Applied and Environmental Microbiology 66(6): 2565-2571 (2000).
Arioli et al. "Gardimycin, a new anitbiotic from *Actinoplanes*: III. Biological properties" The Journal of Antibiotics 29(5):511-515 (1976).
Berge et al. "Pharmaceutical salts" Journal of Pharmaceutical Sciences 66(1):1-19 (1977).
Bierbaum et al. "Cloning, sequencing and production of the lantibiotic mersacidin" FEMS Microbiology Letters 127:121-126 (1995).
Bierman et al. "Plasmid cloning vectors for the conjugal transfer of DNA from *Escherichia coli* to *Streptomyces* spp." Gene 116(1): 43-49 (1992).
Britton et al. "Genome-Wide Analysis of the Stationary-Phase Sigma Factor (Sigma-H) Regulon of *Bacillus subtilis*" Journal of Bacteriology 184(17):4881-4890 (2002).
Castiglione et al. "A novel lantibiotic acting on bacterial cell wall synthesis produced by uncommon actinomycete *Planomonospora* sp." Biochemistry 46:5884-5895 (2007).
Chatterjee et al. "Biosynthesis and Mode of Action of Lantibiotics" Chem. Rev. 105:633-683 (2005).
Coronelli et al. "Gardimycin, A New Antibiotic From Actinoplanes: II. Isolation and preliminary characterization" Journal of Antibiotics 29(5):507-510 (1976).
Cotter et al. "Bacterial lantibiotics: strategies to improve therapeutic potential" Current Protein Peptide Science 6(1):61-75 (2005).
Dabard et al. "Ruminococcin A, a new lantibiotic produced by a *Ruminococcus gnavus* strain isolated from human feces" Appl. Environ. Microbiol. 67:4111-4118 (2001).
Dawson "Lantibiotics as antimicrobial agents" Expert Opinion on Therapeutic Patents, Informa Healthcare, GB, 17(4):365-369 (2007).
de Vos et al. "Maturation pathway of nisin and other lantibiotics: post-translationally modified antimicrobial peptides exported by gram-positive bacteria" Molecular Microbiology 17(3):427-37 (1995).
Dower et al. "High efficiency transformation of *E. coli* by high voltage electroporation" Nucleic Acids Research 16(13):6127-6145 (1988).
Fleisher et al. "Improved oral drug delivery: solubility limitations overcome by the use of prodrugs" Advanced Drug Delivery Reviews 19(2):115-130 (1996).
Flett et al. "High efficiency intergeneric conjugal transfer of plasmid DNA from *Escherichia coli* to methyl DNA-restricting Streptomycetes" FEMS Microbiology Letters 155(2): 223-229 (1997).
Fukase et al. "Synthetic study of peptide antibiotic nisin. V. Total synthesis of nisin" Bull. Chem. Soc. Jpn. 65:2227-2240 (1992).
Fumi et al. "Rifaximin treatment for symptoms of irritable bowel syndrome" The Annals of Pharmacotherapy 42:408-412 (2008).
Gardiner et al. "Fate of the Two-Component Lantibiotic Lacticin 3147 in the Gastrointestinal Tract" Applied and Environmental Microbiology 73(21):7103-7109 (2007).
Gravesen et al. "pbp2229-Mediated nisin resistance mechanism in Listeria monocytogenes confers cross-protection to class IIa bacteriocins and affects virulence gene expression" Applied and Environmental Microbiology 70(3): 1669-1679 (2004).
Guder et al. "Role of the single regulator MrsR1 and the two-component system MrsR2/K2 in the regulation of mersacidin production and immunity" Applied and Environmental Microbiology 68(1):106-113 (2002).
Guiotto et al. "PEGylation of the antimicrobial peptide nisin A: problems and perspectives" Il Farmaco 58(1):45-50 (2003).
Gust et al. "PCR-targeted Streptomyces gene replacement identifies a protein domain needed for biosynthesis of the sesquiterpene soil odor geosmin" PNAS 100(4): 1541-1546 (2003).
Gust et al. "λ Red-mediated genetic manipulation of antibiotic-producing Streptomyces" Advances in Applied Microbiology 54:107-128 (2004).
Heinzelmann et al. "A glutamate mutase is involved in the biosynthesis of the lipopeptide antibiotic friulimicin in Actinoplanes friuliensis" Antimicrobial Agents and Chemotherapy 47(2): 447-457 (2003).
Hilger et al. "Differential binding of IgG and IgA antibodies to antigenic determinants of bovine serum albumin" Clin. Exp. Immunol 123:387-394 (2001).
Holtsmark, et al. "Purification, Characterization, and Gene Sequence of Michiganin A, an Actagardine—Like Lantibiotic Produced by the Tomato Pathogen *Clavibacter michiganensis* subsp. *michiganensis*" Applied and Environmental Microbiology 72(9):5814-5821 (2006).
Jack et al. "The genetics of lantibiotic biosynthesis" BioEssays 17(9): 793-802 (1995).
Kettenring et al. "Sequence determination of actagardine, a novel lantibiotic, by homonuclear 2D NMR spectroscopy" J. Antibiot. 43(9):1082-1088 (1990).
Lonetto et al. "The sigma 70 family: sequence conservation and evolutionary relationships" Journal of Bacteriology 174(12): 3843-3849 (1992).
Louie et al. "A phase 2 study of the toxin binding polymer tolevamer in patients with *C. difficile* associated diarrhoea" Proceedings of 14th European Congress of Clinical Microbiology and Infectious Diseases, Prague Congress Centre, Prague, Czech Republic, p. 548 (May 1-4, 2004).
Louie et al. "Tolemaver (GT160-246) binds *Clostridium cytotoxins* A/B and is associated with restoration of components of the anaerobic intestinal microflora during treatment of C. difficileassociated diarrhoea" Proceedings of 14th European Congress of Clinical Microbiology and Infectious Diseases, Prague Congress Centre, Prague, Czech Republic, p. 855 (May 1-4, 2004).
Malabarba et al. "Physico-chemical and biological properties of actagardine and some acid hydrolysis products" The Journal of Antibiotics 38(11):1506-1511 (1985).
Malabarba et al. "Synthesis and biological activity of some amide derivatives of the lantibiotic actagardine" The Journal of Antibiotics 43(9):1089-1097 (1990).
Marahiel et al. "Regulation of peptide antibiotic production in *Bacillus*" Molecular Microbiology 7(5):631-636 (1993).
McClerren et al. "Discovery and in vitro biosynthesis of haloduracin, a two-component lantibiotic" PNAS 103(46):17243-17248 (2006).
Miner et al. "Steroid-refractory ulcerative colitis treated with corticosteroids, metronidazole and vancomycin: a case report" BMC Gastroenterology 5:3 (2005).
O'Sullivan et al. "High- and low-copy-number Lactococcus shuttle cloning vectors with features for clone screening" Gene 137:227-231 (1993).
Parenti et al. "Gardimycin, a new antibiotic from Actinoplanes. I. Description of the producer strain and fermentation studies" The Journal of Antibiotics 29(5):501-506 (1976).

Rea et al. "Antimicrobial activity of lacticin 3147 against clinical Clostridium difficile strains" Journal of Medical Microbiology 56:940-946 (2007).

Rey et al. "Complete genome sequence of the industrial bacterium *Bacillus licheniformis* and comparisons with closely related *Bacillus* species" Genome Biology 5(10):R77 (2004).

Sahl et al. "Lantibiotics: Biosynthesis and biological activities of uniquely modified peptides from gram-positive bacteria" Ann. Rev. Microbiology 52:41-79 (1998).

Somma et al. "Gardimycin, a new antibiotic inhibiting peptidoglycan synthesis" Antimicrobial Agents and Chemotherapy 11(3):396-401 (1977).

Szekat et al. "Construction of an expression system for site-directed mutagenesis of the lantibiotic mersacidin" Applied and Environmental Microbiology 69(7):3777-3783 (2003).

"Treatment of *Clostridium difficile*—Associated Disease (CDAD)" Obstetrics and Gynecology 109(4):993-995 (2007).

Turner et al. "Solution structure of plantaricin C, a novel lantibiotic" Eur. J. Biochem. 264:833-839 (1999).

Turtell et al. "The use of nisin in cheesemaking. Chapter 5: International acceptance of nisin as a food preservative" Bulletin of the Int. Dairy Fed. 329:20-23 (1988).

Ugurlu et al. "Colonic delivery of compression coated nisin tablets using pectin/HPMC polymer mixture" Eur. J. Pharm. Biopharm. 67:202-210 (2007).

van Kraaij et al. "Lantibiotics: biosynthesis, mode of action and applications" Nat. Prod. Rep. 16:575-587 (1999).

Vértesy et al. "Ala(0)-actagardine, a new lantibiotic from cultures of Actinoplanes liguriae ATCC 31048" Journal of Antibiotics (Tokyo) 52(8):730-741 (1999).

Zimmermann et al. "The tetracyclic lantibiotic actagardine. 1H-NMR and 13C-NMR assignments and revised primary structure" Eur. J. Biochem. 228:786-797 (1995).

Zimmermann et al. "The three-dimensional solution structure of the lantibiotic murein-biosynthesis-inhibitor actagardine determined by NMR" Eur. J. Biochem. 246:809-819 (1997).

Appleyard et al. "NVB302 : Gastrointestinal Stability and in vivo Activity in the Hamster Cecitis Model for *Clostridium difficile* Infection," Poster F1-1520, 49th ICAAC, Sep. 12-15, 2009, San Francisco, USA.

Appleyard et al. "NVB302: A Narrow Spectrum Antibiotic under Development for the Treatment of *Clostridium difficile* Infection," Poster F1-1517, 49th ICAAC, Sep. 12-15, 2009, San Francisco, USA.

Berendsen, "A Glimpse of the Holy Grail?" Science, 1998, 282, pp. 642-643.

Boakes et al., "Organization of the genes encoding the biosynthesis of actagardine and engineering of a variant generation system," Molecular Microbiology, 2009, 72(5), pp. 1126-1136.

Bradley et al. "Limits of Cooperativity in a Structurally Modular Protein: Response of the Notch Ankyrin Domain to Analogous Alanine Substitutions in Each Repeat," J. Mol. Biol., 2002, 324, pp. 373-386.

Definition of moiety, from http://dictionary.reference.com/browse/moiety, pp. 1-3. Accessed Aug. 26, 2010.

Designing Custom Peptides, from SIGMA Genosys, pp. 1-2. Accessed Dec. 16, 2004.

European Examination for European Patent Application No. 07704921.1 dated Aug. 30, 2010.

International Search Report and Written Opinion for PCT/GB2010/000042 dated May 20, 2010.

International Search Report and Written Opinion for PCT/GB2010/000188 dated May 20, 2010.

New Zealand Examination Report on New Zealand Patent Application 569486 dated Apr. 27, 2010.

Ngo et al. "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Rudinger J, "Characteristics of the amino acids as components of a peptide hormone sequence," Peptide Hormones, JA Parsons Edition, University Park Press, Jun. 1976, pp. 1-7.

Schinzel R, Drueckes P, "The phosphate recognition site of *Escherichia coli* maltodextrin phosphorylase," FEBS, Jul. 1991, 286(1,2), pp. 125-128.

Translation of Israeli Examination Report on Israeli Patent Application No. 192446 dated Apr. 22, 2010.

Voet et al. "Abnormal Hemoglobins," Biochemistry, Second Edition, John Wiley & Sons, Inc., 1995, pp. 235-241.

Wadman et al. "NVB302: In vitro Activity Against Clostridium difficile and Intestinal Strains of Anaerobic Bacteria," Poster F1-1518, 49th ICAAC, Sep. 12-15, 2009, San Francisco, USA.

Written Opinion of the International Preliminary Examining Authority in PCT/GB2010/000043, dated Feb. 1, 2011.

European Search Report issued in European Patent Application No. EP 10 00 0424 (Apr. 1, 2010).

European Examination issued in European Patent Application No. 07 704 921.1 (Apr. 4, 2010).

International Search Report and Written Opinion in PCT/GB2010/000043 (Mar. 29, 2010).

Widdick et al., "Cloning and engineering of the cinnamycin biosynthetic gene cluster from *Streptomyces cinnamoneus cinnamoneus* DSM 40005", PNAS, 100(7):4316-4321 (Apr. 1, 2003).

\* cited by examiner (a)

(b)

(c)

(a)

(b)

(a)

(b)

LANTIBIOTIC-BASED COMPOUNDS HAVING ANTIMICROBIAL ACTIVITY

RELATED APPLICATIONS

The present application is a U.S. National Phase Application of International Application No. PCT/GB2008/002465, filed Jul. 18, 2008, which claims the benefit of Great Britain Patent Application No. 0714029.6, filed Jul. 18, 2007, which is hereby incorporated by reference in its entirety.
Sequence Listing Submission via EFS-Web A computer readable text file, entitled "056646-5047-SequenceListing.txt," created on or about Jan. 15, 2010 with a file size of about 15 kb contains the sequence listing for this application and is hereby incorporated by reference in its entirety.

FIELD OF THE INVENTION

This invention relates to lantibiotic-based compounds having antimicrobial activity, the methods for their production, and their use.

BACKGROUND

The lanthionine-containing antibiotic peptides, or "lantibiotics", are a group of natural products secreted by various Gram-positive bacteria. The defining structural feature of this class of compounds is the presence of the thioether amino acids lanthionine and methyllanthionine, formed via specialised biosynthetic pathways acting on ribosomally synthesised, linear peptide precursors.

Lantibiotics have been classified into two classes, type-A and type-B. Type-A lantibiotics are generally elongate amphiphiles that retain substantial linear sections in their structure. Examples of type-A lantibiotics are nisin and subtilin. Nisin and related molecules can bind to lipid II, an indispensible intermediate in bacterial cell wall synthesis. In addition, the type-A lantibiotics are capable of forming pores in plasma membranes. The potent antimicrobial activity of the type-A lantibiotics is thought to derive from the combination of their lipid II binding and pore forming capabilities.

Type-B lantibiotics are generally smaller peptides that are folded and cross-linked into globular shapes and lack extensive linear peptide sections. Examples of type-B lantibiotics are Mersacidin, Actagardine and Cinnamycin. Like the type-A lantibiotics they have antimicrobial activity that is believed to derive mainly from their ability to bind to Lipid II, as they are not capable of forming pores in the bacterial membranes.

Mersacidin and actagardine have potent antibacterial activity against a range of Gram-positive organisms including *Streptococcus, Enterococcus* and *Clostridium* species.

For reviews, see Sahl and Bierbaum (1998) Annual Rev. Microbiol. 52:41-79; van Kraaij, de Vos, Siezen and Kuipers, Nat. Prod. Rep. 1999, 16, 575; Chatterjee, Paul, Xie and van der Donk, Chem. Rev. 2005, 105, 633.

Actagardine and analogues have been reported to be produced by two species of Actinoplanes; *A. garbadinensis* and *A. liguriae* [Parenti, Pagani, Beretta, J. Antibiotics, 1976, 29, 501; U.S. Pat. No. 6,022,851]. Actagardine is produced from a pre-pro-peptide, the C-terminal portion of which has the polypeptide sequence of SSGWVCTLTIECGTVICAC. This polypeptide is modified by the following crosslinks, creating secondary and tertiary structure: crosslink 1-6, Lanthionine (Ser-Cys); crosslink 7-12, Beta-methyllanthionine (Thr-Cys); crosslink 9-17, Beta-methyllanthionine (Thr-Cys); crosslink 14-19, Beta-methyllanthionine sulfoxide (Thr-Cys). Also co-produced is an analogue [Zimmerman, Metzger and Jung, Eur. J. Biochem 1995, 228, 786] in which the crosslink 14 and 19 is not oxidized i.e. it is a beta-methyllanthionine not betamethyllanthionine sulfoxide which is named herein deoxyactagardine.

A further variant, herein called deoxyactagardine B, derived from a propeptide with a C-terminal sequence SSGWVCTLTIECGTLVCAC and lacking a sulphoxide on the crosslink between residues 14 and 19 has also been isolated from *A. liguriae* (as discussed in co-pending application PCT/GB2007/000138 (WO/2007/083112), which is herein incorporated by reference).

The structures of actagardine and deoxyactagardine B are shown below.

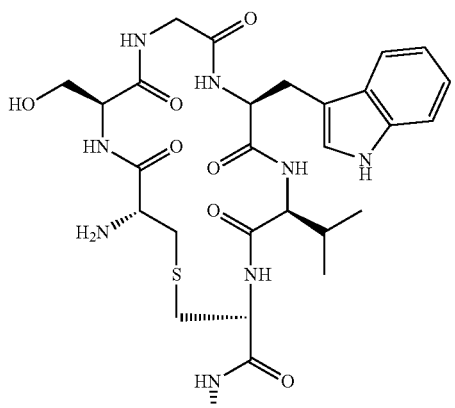

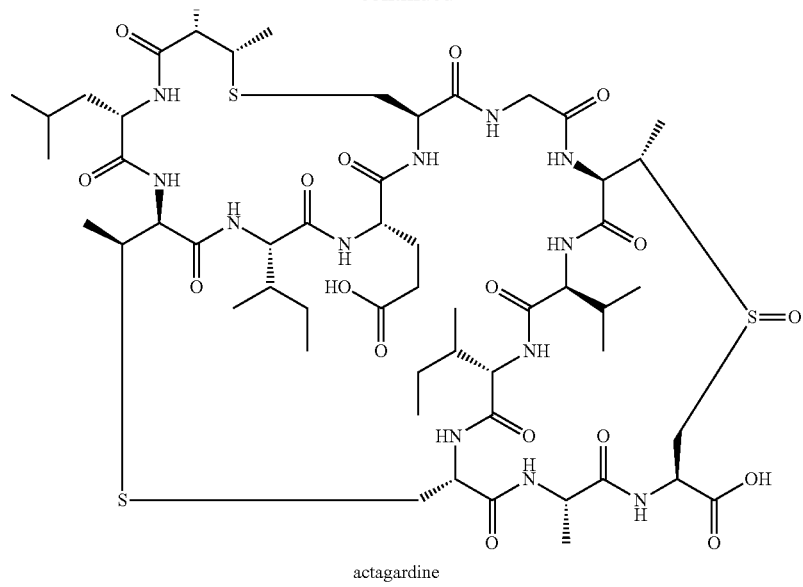
actagardine
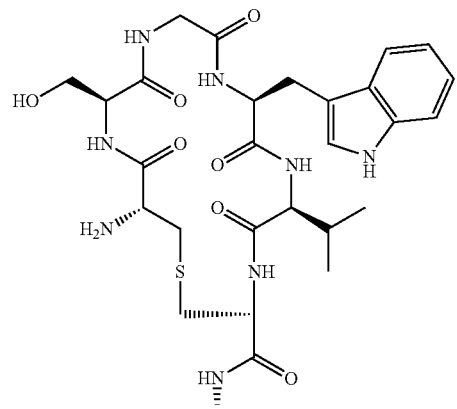
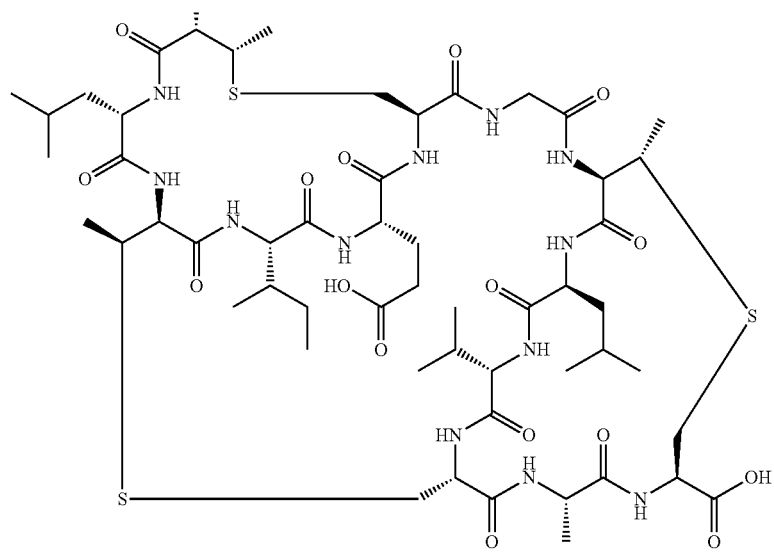
deoxyactagardine B

U.S. Pat. No. 6,022,851 describes the isolation of actagardine and related forms from isolated strains of *A. garbadinensis* and *A. liguriae*.

DISCLOSURE OF THE INVENTION

The present invention relates to lantibiotic-based compounds having antimicrobial activity, the methods for their production, and their use. These compounds have a similar spectrum of anti-microbial activity to actagardine and provide new and useful alternatives to this lantibiotic. In one aspect, the present invention provides novel derivatives of actagardine, actagardine B and deoxyactagardine B. In another aspect, the lantibiotic-based compounds of the invention are prepared by modification of the C-terminus, and optionally the N-terminus, of lantibiotics, and lantibiotic variants and derivatives. The compounds of the invention may have improved antimicrobial activity in comparison to the actagardine, actagardine B and deoxyactagardine B compounds from which they are derived.

The invention also provides pharmaceutical compositions comprising a compound of the invention together with a pharmaceutically acceptable carrier or diluent.

In a further aspect, the present invention provides the use of the compounds and compositions of the invention in therapy. Particularly, the present invention provides methods for the treatment or prophylaxis of a microbial infection in a subject, the methods comprising administering to said subject a compound or composition of the invention. The compound or composition may be administered orally, rectally, intravenously, vaginally, intramuscularly or topically. Most preferably the compounds and compositions of the invention are administered orally. The infection may be a bacterial infection. Preferably, the infection is a *Clostridium* infection, preferably a *Clostridium perfringens*, *Clostridium difficile*, *Clostridium tetani* or *Clostridium botulinum* infection, most preferably *C. difficile* infection. These methods provide new and useful alternatives to methods of treatment utilising a type-A lantibiotic, vancomycin or metronidazole.

The compounds described herein, and derivatives and variants thereof, may be selective for *C. difficile*. These compounds may have reduced activity against other commensal gut flora, particularly *Bifidobacterium* spp and *Bacteroides* spp, compared to vancomycin or metronidazole.

The compounds described herein have similar activity against *C. difficile* as vancomycin and provide new and useful alternatives to vancomycin in a method of treatment or prophylaxis of a microbial infection in a subject.

The compounds described herein may have increased stability to enzymatic degradation compared to nisin. Particularly, the compounds may have improved stability to intestinal juices compared to nisin. The type-B lantibiotic structures, upon which the present compounds are based, are more compact than type-A compounds and they do not have the extensive linear character of the A-forms. Consequently, they are less vulnerable to proteolysis and are therefore more likely to reach the site of an infection, such as a bacterial infection of the lower intestinal tract.

The invention also provides the use of the compounds and compositions of the invention as antimicrobials for use in vivo or in vitro.

In a further aspect, the present invention provides methods for synthesising compounds of the invention from a lantiobiotic or variants and/or derivatives thereof.

BRIEF DESCRIPTION OF THE DRAWINGS

FIGS. 3 (*a*) to (*c*) show the conversion of deoxyactagardine B to the monoamide Compound I and a small amount of the diamide during the course of the reaction.

DETAILED DESCRIPTION OF THE INVENTION

Figure 1:
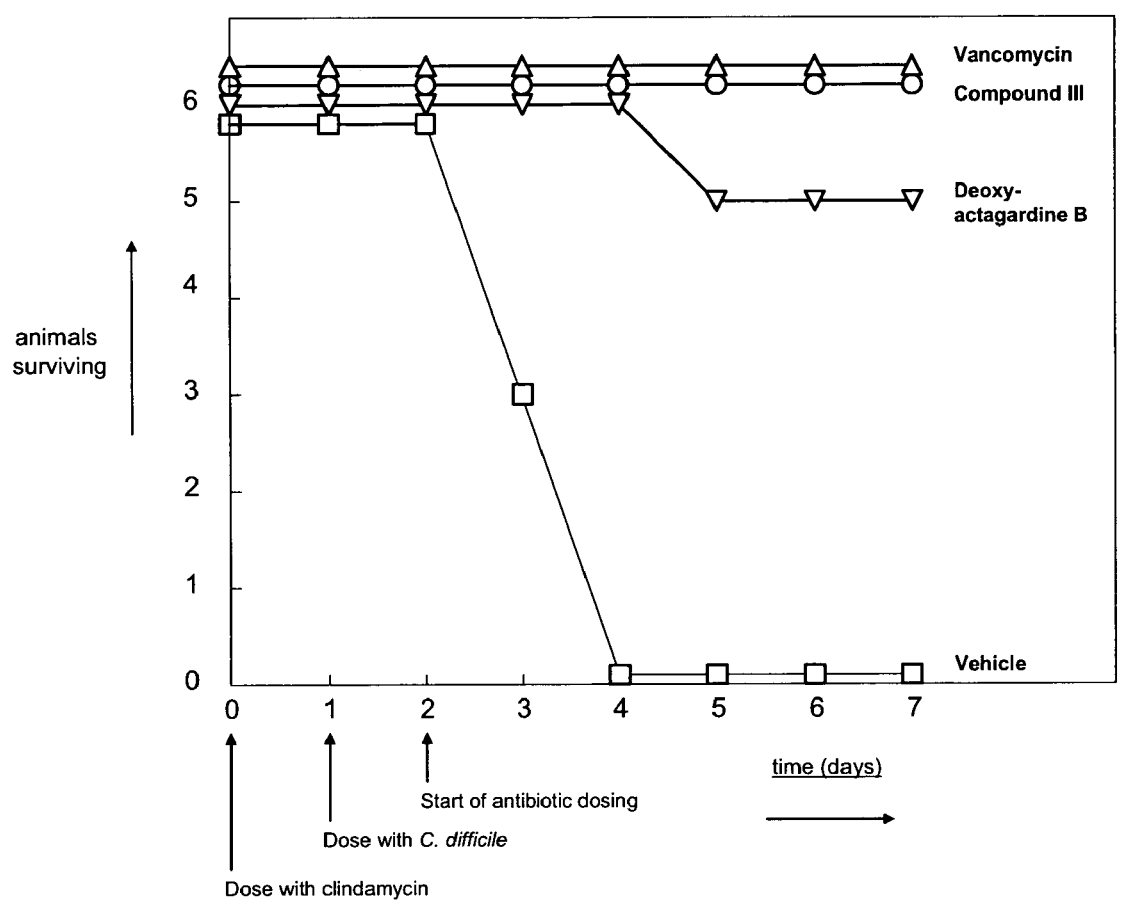
FIG. 1 shows the efficacy in vivo of compound III in the hamster model of *C. difficile*-associated cecitis.

The present invention relates to compounds based on lantibiotics, particularly type-B lantibiotics such as actagardine, actagradine B and deoxy-actagardine B.

The lantibiotic-based compounds provided herein may have improved solubility and/or other physicochemical properties and/or biological activity compared to the parent lantibiotics from which they are derived. Improved solubility has significant advantages for the purposes of formulation of the compounds of the invention for the purpose of oral and intravenous administration. Furthermore, improved solubility allows for higher concentrations of antibiotic to be present at the site of action, potentiating greater efficacy.

Compounds

In a first aspect of the present invention there is provided a compound of formula (I):

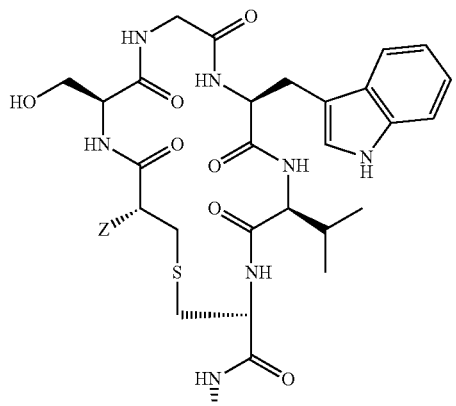

-continued

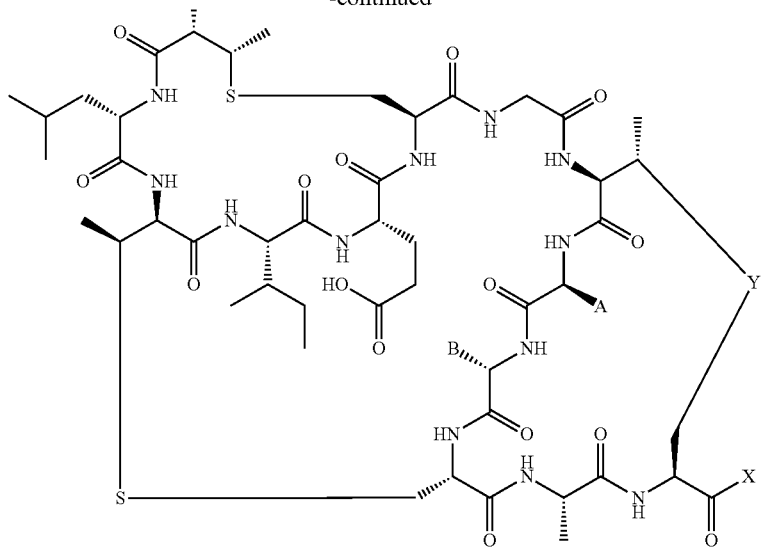

wherein A is a Leu; Val; or Ile amino acid side chain; B is a Leu; Val; or Ile amino acid side chain; X is —NR$^1$R$^2$; and Y, Z, R$^1$ and R$^2$ are as defined below, or a pharmaceutically acceptable salt thereof.

Alternatively, the structure of the compound may be represented conveniently thus:

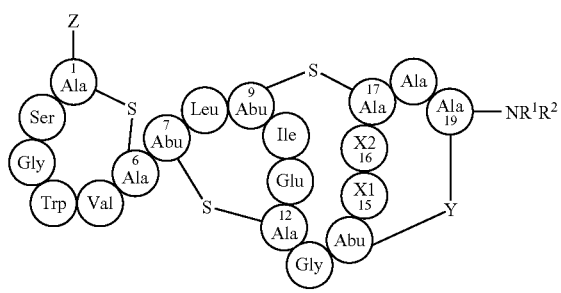

wherein:
X1 denotes that the residue is Leu; Val; or Ile;
X2 denotes that the residue is Leu; Val; or Ile;
R$^1$ represents an alkyl or heteroalkyl group, substituted by at least one hydroxyl substituent, and R$^2$ represents hydrogen, or an alkyl or heteroalkyl group, optionally substituted by at least one hydroxyl substituent, or W and R$^2$ taken together with the nitrogen atom represent a heterocyclic group having at least one hydroxyl substituent, wherein the heterocyclic group optionally further contains one or more heteroatoms;
Z is an amino acid residue, —NR$^3$R$^4$, —NR$^5$COR$^6$, —NR$^5$C(O)OR$^6$; —NR$^5$SOR$^6$, —NR$^5$SO$_2$R$^6$; —NR$^5$C(S)NR$^6$R$^7$, —NR$^5$C(NR$^8$)NR$^6$R$^7$, or —N=R$^9$, where R$^3$, R$^4$, R$^5$, R$^6$, R$^7$, R$^8$ and R$^9$ are independently hydrogen, or a group, optionally substituted, selected from alkyl, heteroalkyl, aryl, heteroaryl, aralkyl and heteroaralkyl, with the proviso that R$^9$ is not hydrogen;
Y is —S— or —S(O)—;
or a pharmaceutically acceptable salt thereof. In a further aspect, the invention provides variants and biologically active derivatives of these compounds.

DEFINITIONS

It will be understood by reference to Z being a group —NH$_2$, that this moiety represents the N-terminus of the alanine residue at position 1 of the above compound. By reference to the group Z being an amino acid residue, it will be understood that this moiety represents an amino acid, conventionally referred to in the art as Xaa(0), linked to the alanine at position 1 via an amide bond. By reference to the group Z being —NR$^3$R$^4$, —NR$^5$COR$^6$, —NR$^5$C(O)OR$^6$; —NR$^5$SOR$^6$, —NR$^5$SO$_2$R$^6$; —NR$^5$C(S)NR$^6$R$^7$, —NR$^5$C(NR$^8$)NR$^6$R$^7$, or —N=R$^9$, it will be understood that these groups represent modifications of the N-terminus of the alanine at position 1.

In the representation above it will be appreciated that the amino acid residues are denoted by the appropriate three letter code. Abu refers to a 4-aminobutyric acid-derived amino acid residue, as will be clear from the structural formula.

It will also be understood by reference to the group —NR$^1$R$^2$ (—X), that this moiety represents a group linked to the alanine residue at position 19 via an amide bond, i.e. where the nitrogen atom to which R$^1$ and R$^2$ is attached forms part of the amide bond. It will be understood that this group represents a modification of the C-terminus of the alanine at position 19.

It will also be appreciated that a reference to Z being an amino acid residue is a reference to a group —NR$^6$COR$^6$ where R$^6$ represents the amino- and side chain-functionality of an amino acid residue. For example, for the amino acid residue glycine, R$^6$ is —CH$^2$NH$_2$. Typically, for an amino acid residue, R$^6$ is a C$_{1-7}$, alkyl group having an amino substituent and optionally further substituted as appropriate.

Where X1 and X2 are Val and Ile respectively, and Y is —S(O)—, the compound may be referred to as an actagardine derivative.

Where X1 and X2 are Leu and Val respectively, and Y is —S—, the compound may be referred to as a deoxy-actagardine B derivative.

Where X1 and X2 are Leu and Val respectively, and Y is —S—, Z is —NH$_2$, R$^1$ is —CH$_2$CH$_2$OH and R$^2$ is hydrogen, the compound is also referred to as deoxy-actagardine B N-[2-ethanolamine]monocarboxamide.

Alkyl: The term "alkyl" as used herein, pertains to a monovalent moiety obtained by removing a hydrogen atom from a carbon atom of a hydrocarbon compound having from 1 to 20 carbon atoms (unless otherwise specified) and which may be saturated or unsaturated (e.g. partially unsaturated, fully unsaturated).

Heteroalkyl: The term "Heteroalkyl" as used herein refers to an alkyl group having one or more carbon atoms replaced with a N, S, or O heteroatom.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $Cl_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include, but are not limited to, iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_s$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N2O_1$: oxadiazine ($C_6$);

$O_1S_1$: oxathiole ($C_5$) and oxathiane (thioxane) ($C_5$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_s$), such as allopyranose, altropyranose, glucopyranose, mannopyranose, gulopyranose, idopyranose, galactopyranose, and talopyranose.

$R^1$ and $R^2$ taken together with the nitrogen atom of the amide bond may represent a heterocyclyl group having at least one hydroxyl substituent. The heterocyclyl group may be a group selected from the $N_1$ examples provided above. The heterocyclyl group may contain one or more further heteroatoms. The heterocyclyl group may then be a group selected from the $N_2$, $N_1O_1$, $N_1S_1$, $N_2O_1$ and $N_1O_1S_1$ examples provided above.

Aryl: the term "aryl" as used herein, refers to a monovalent moiety obtained by removing a hydrogen atom from an aromatic ring atom of an aromatic compound, said compound having one ring, or two or more rings (e.g., fused).

Heteroaryl: The term "Heteroaryl" as used herein refers to an aryl group having one or more carbon atoms replaced with, but not limited to, a N, S, O heteroatom. In this case, a group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Aralkyl: The term aralkyl as used herein, refers to an alkyl group, as defined above, substituted with one or more, preferably one, aryl groups as defined above.

Heteroaralkyl: The term 'heteroaralky' as used herein, refers to an alkyl group, as defined above, substituted with one or more, preferably one, aryl groups as defined above, where one or more carbon atoms in the alkyl and/or aryl group have been replaced with, but not limited to, a N, S, O heteroatom.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound and having from 5 to 20 ring atoms, and wherein at least one of said ring(s) is an aromatic ring. Preferably, each ring has from 5 to 7 ring atoms.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above groups, whether alone or part of another substituent, may themselves optionally be substituted with one or more groups selected from themselves and the additional substituents listed below.

Halo: —F, —Cl, —Br, and —I.
Hydroxyl: —OH.
Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.
Nitro: —$NO_2$.
Cyano (nitrile, carbonitrile): —CN.
Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ arylgroup (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).
Carboxy (carboxylic acid): —COOH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)$OCH_3$, —C(=O)$OCH_2CH_3$, —C(=O)OC($CH_3$)$_3$, and —C(=O)OPh.
Amido(carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(O)$NH_2$, —C(=O)$NHCH_3$, —C(=O)N($CH_3$)$_2$, —C(=O)$NHCH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.
Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —$NHCH_3$, —NHCH($CH_3$)$_2$, —N($CH_3$)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.
Acylamido (acylamino): —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

succinimidyl    maleimidyl    pthalimidyl

Aminocarbonyloxy: —OC(=O)$NR^1R^2$, wherein $R^1$ and $R^2$ are independently amino substituents, as defined for amino groups. Examples of aminocarbonyloxy groups include, but are not limited to, —OC(=O)$NH_2$, —OC(=O)NHMe, —OC(=O)$NMe_2$, and —OC(=O)$NEt_2$.

Ureido: —N($R^1$)CONR$^2$R$^3$ wherein $R^2$ and $R^3$ are independently amino substituents, as defined for amino groups, and R1 is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —$NHCONH_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHCONHPh.

Guanidino: —NH—C(=NH)$NH_2$.
Tetrazolyl: a five membered aromatic ring having four nitrogen atoms and one carbon atom, Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)$NH_2$, —C(=NH)$NMe_2$, and —C(=NMe)$NMe_2$.

Nitro: —$NO_2$.
Nitroso: —NO.
Azido: —$N_3$.
Cyano (nitrile, carbonitrile): —CN.
Isocyano: —NC.
Cyanato: —OCN.
Isocyanato: —NCO.
Thiocyano (thiocyanato): —SCN.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Isothiocyano (isothiocyanato): —NCS.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$alkyl group, a $C_{3-20}$heterocyclyl group, or a $C_{5-20}$ aryl group, preferably a $C_{1-7}$ alkyl group (also referred to herein as $C_{1-7}$alkyl disulfide). Examples of $C_{1-7}$alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$alkyl group, a $C_{3-20}$ heterocyclyl group, or a $C_{5-20}$aryl group, preferably a $C_{1-7}$ alkyl group. Examples of sulfine groups include, but are not limited to, —S(=O)CH$_3$ and —S(=O)CH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$heterocyclyl group, or a $C_{5-20}$ aryl group, preferably a $C_{1-7}$ alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonyloxy: —OS(=O)$_2$R, wherein R is a sulfonyloxy substituent, for example, a $C_{1-7}$ alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$alkyl group, a $C_{3-20}$heterocyclyl group, or a $C_{3-20}$aryl group, preferably a $C_{1-7}$alkyl group or a $C_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR)$^2$NR$^2{}_2$, where R$^1$ and R$^2$ are phosphoramidite substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2{}_2$, where R$^1$ and R$^2$ are phosphoramidate substituents, for example, —H, a (optionally substituted) $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Silyl: —SiR$_3$, where R is a silyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of silyl groups include, but are not limited to, —SiH$_3$, —SiH$_3$), —SiH(CH$_3$)$_2$, —Si(CH$_3$)$_3$, —Si(Et)$_3$, —Si(iPr)$_3$, —Si(tBu)(CH$_3$)$_2$, and —Si(tBu)$_3$.

Oxysilyl: —Si(OR)$_3$, where R is an oxysilyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of oxysilyl groups include, but are not limited to, —Si(OH)$_3$, —Si(OMe)$_3$, —Si(OEt)$_3$, and —Si(OtBu)$_3$.

Siloxy (silyl ether): —OSiR$_3$, where SiR$_3$ is a silyl group, as discussed above.

Oxysiloxy: —OSi(OR)$_3$, wherein OSi(OR)$_3$ is an oxysilyl group, as discussed above.

In many cases, substituents are themselves substituted.

As mentioned above, the groups that form the above listed substituent groups, e.g. alkyl, heterocyclyl and aryl, may themselves be substituted. Thus, the above definitions cover substituent groups which are substituted.

Preferred Compounds

Preferred compounds of the first aspect of the invention are described below.

Preferably, X1 is Leu, and X2 is Val or Ile; or X1 is Val, and X2 is Val or Ile. Most preferably, X1 is Leu, and X2 is Val; or X1 is Val, and X2 is Ile.

R$^1$, R$^2$, R$^3$, R$^4$, R$^5$, R$^6$, R$^7$, R$^8$, R$^9$ and R$^{10}$ may be optionally substituted or optionally further substituted as appropriate. However, in some embodiments these groups are unsubstituted or not further substituted as appropriate.

Where R$^1$ or R$^2$ is an alkyl group, the alkyl group may be a $C_{1-7}$ alkyl group, most preferably a $C_{1-4}$ alkyl group. The R$^1$ or R$^2$ alkyl group is preferably fully saturated.

R$^1$ or R$^2$ may have one, two, three, four, five, six or seven carbon atoms.

Where R$^1$ and R$^2$ taken together with the nitrogen atom of the amide represent a heterocyclic group where the group further contains one or more heteroatoms, preferably the heteroatoms are not at neighbouring positions in the heterocyclic ring.

Where R$^1$ and R$^2$ taken together with the nitrogen atom of the amide represent a heterocyclic group where the group further contains one or more heteroatoms, the heterocyclic group is preferably a $C_{3-20}$ heterocyclic group. Preferably the heterocyclic group is a $C_{5-10}$ heterocyclic group. The heterocyclic group may have 5, 6 or 7 ring atoms.

Both R$^1$ and R$^2$ may have one or more hydroxyl substituents. Between them, R$_1$ and R$^2$ may have two or more hydroxyl substituents. Preferably, R$^1$ has one, two or three hydroxyl substituents.

R$^1$ and R$^2$ may be the same.

Preferably R$^1$ is an alkyl group. Preferably R$^2$ is hydrogen.

Where R$^1$ or R$^2$ is a heteroalkyl group having a hydroxyl substituent, the hydroxyl substituent is a substituent on a carbon atom of the heteroalkyl group.

Where R$^1$ or R$^2$ is an alkyl or heteroalkyl group having two or more hydroxyl substituents, each hydroxyl substituent is a substituent on a different carbon atom of the alkyl or heteroalkyl group.

In one embodiment, the R$^1$ or R$^2$ alkyl group is acyclic. In one embodiment, the R$^1$ or R$^2$ alkyl group is linear.

In one embodiment, R$^1$ or R$^2$ is substituted or further substituted as appropriate. The substituent may be one or more groups selected from the group consisting of: carboxy, ester, acyloxy, amido, acylamido, and aryl and heteroaryl. Preferably, the substituent is one or more groups selected from the group consisting of: carboxy, ester, acyloxy, aryl and heteroaryl.

Preferably R$^1$ or R$^2$ is independently one of the substituents given below, where * indicates the point of attachment to the nitrogen atom:

Additionally, or alternatively, R$^1$ or R$^2$ may be independently selected from one of the substituents given below, where * indicates the point of attachment to the nitrogen atom:

In one embodiment, R$^1$ is independently selected from one of the substituents given in either of the sets of substituents above. In this embodiment, R$^2$ is preferably hydrogen.

Alternatively, R$^1$ and R$^2$ together with the nitrogen atom, i.e. X, may be a substituent selected from the group below, where * indicates the point of attachment to the C-terminus carbonyl carbon:

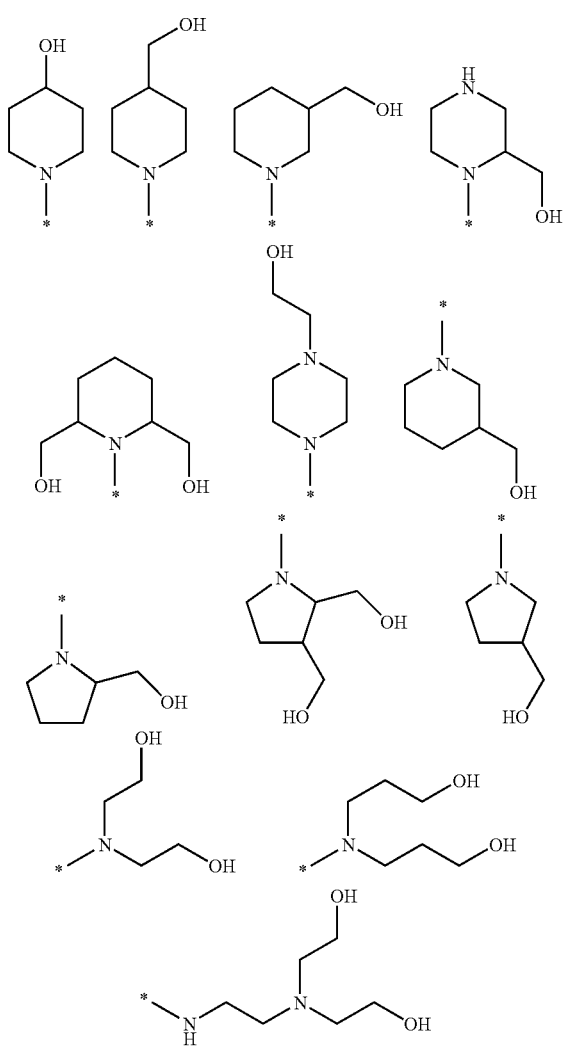

Additionally, or alternatively, $R^1$ or $R^2$ may be independently selected from the substituent given below, where * indicates the point of attachment to the nitrogen atom:

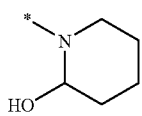

Preferably $R^1$ is —CH$_2$CH$_2$OH.

In one embodiment, Z is —NH$_2$, an amino acid or —NR$^5$COR$^6$. Preferably, Z is —NH$_2$, or an amino acid.

In one embodiment, Z is —NR$^5$COR$^6$ and $R^5$ is hydrogen.

Where Z is an amino acid residue, the amino acid residue is preferably a naturally occurring amino acid residue encoded by the genetic code or its D-isoform, more preferably an amino acid residue selected from the group Ile-, Lys-, Phe-, Val-, Glu-, Asp-, His-, Leu, Arg-, Ser- and Trp-. In one aspect, the amino acid residue may be selected from the group Ile-, Lys-, Phe-, Val-, Glu-, Asp-, His-, Leu-, Arg- and Ser-. Such variants may be produced by chemical addition of the residue to compounds where Z is —NH$_2$, as described in U.S. Pat. No. 6,022,851, which is incorporated herein by reference. It will be appreciated that the chemical addition of an amino acid allows the amino acid to be in the L- or D-configuration. This includes D-Ala, in addition to the D-forms of other amino acids such as those mentioned above.

The amino acid residue may a modified natural amino acid residue, such as those residues formed during the post-translational modification of, for example, serine, cytseine and threonine residues. A residue within the compound of the invention may be selected from the dehydrated amino acids shown in the group below:

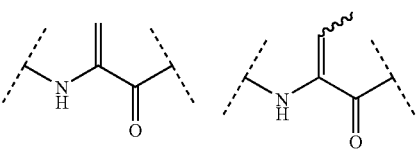

The second of these structures may be referred to as a dehydroamino butyric acid residue. Additionally, an amino acid residue may be selected from the cyclic residues shown in the group below:

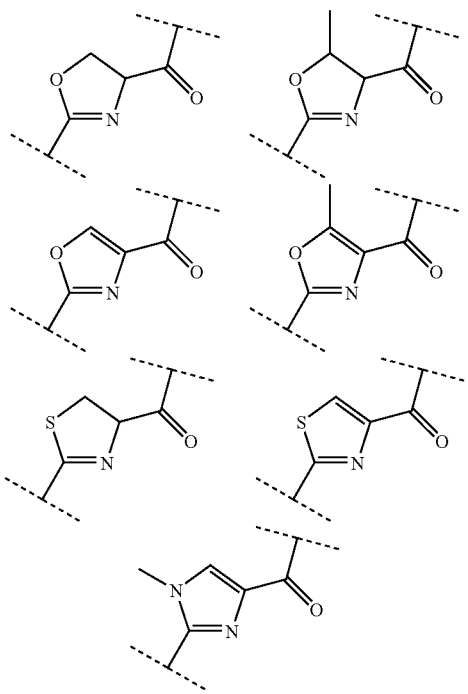

As will be appreciated, the synthesis of these cyclic structures typically involves the cyclisation of a serine, threonine or cysteine residue side chain with an amidic carbonyl of, typically, but not essentially, a neighbouring amino acid residue.

Thus, the structures shown above include a portion of a neighbouring group, such as a neighbouring amino acid. Alternatively, the neighbouring group may be derived from a group that together with a serine, threonine or cysteine residue forms an amide bond at the residue N-terminus. This is shown retrosynthetically in the example below for an oxazoline amino acid residue derived from a serine residue that is linked with a neighbouring group through an amide bond at the N-terminus of the serine residue:

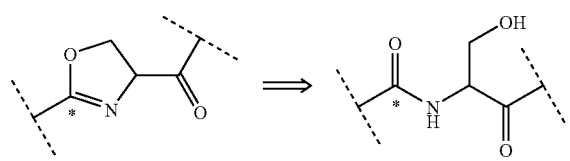

The asterisk (*) indicates the location of the carbon atom in the oxazoline as derived from the carbonyl carbon in the neighbouring group. The retrosynthesis is presented for illustrative purposes only, and the post translationally modified amino acid residues discussed above may be prepared from alternative precursors.

The amino acid residue may be a non-natural or unusual natural amino acid. The amino acid may be selected from the group consisting of seleno serine, aminobutyric acid, aminoisobutyric acid, butlyglycine, citrulline, cyclohexylalanine, diaminopropionic acid, homoserine, hydroxy proline, norleucine, norvaline, ornithine, penicillaminepyroglutamic acid, sarcosine, statine, tetrahydroisoquinoline-3-carboxylic acid, and thienylalanine. The L- or D-forms may be selected.

The amino acid may be an α-, β-, or γ-amino acid. The amino group of the amino acid may be mono- or di-alkylated. Where Z is an amino acid residue, the amino group of the amino acid may be modified. Thus, the N terminus may be a group selected from $-NR^3R^4$, $-NR^5COR^6$, $-NR^5SOR^6$; $-NR^5SOR^6$, $-NR^5SO_2R^6$; $-NR^5C(S)NR^6R^7$ and $-NR^5C(NR^8)NR^6R^7$ where $R^3$, $R^4$, $R^5$, $R^6$, $R^7$ and $R^8$ are defined as above.

Where Z is an amino acid residue, the amino acid residue may also be a protected amino acid residue. The amino group such protecting groups may be selected from the group consisting of Fmoc, Boc, Ac, Bn and Z (or Cbz). The side-chain may also be protected as appropriate. The side chains protecting groups may be selected from the group consisting of Pmc, Pbf, OtBu, Trt, Acm, Mmt, tBu, Boc, ivDde, 2-ClTrt, tButhio, Npys, Mts, $NO_2$, Tos, OBzl, OcHx, Acm, pMeBzl, pMeOBz, OcHx, Born, Dnp, 2-Cl—Z, Bzl, For, and 2-Br—Z as appropriate for the side chain.

Natural and non natural amino acids, and their protected versions, as well as protecting group deprotection strategies are well known. Many are summarised in the Merck Novabiocher™ catalog '*Reagents for Peptide and High-Throughput Synthesis*' (2006/7) (incorporated herein by reference in its entirety).

One of $R^3$ and $R^4$ may be a group, optionally substituted, selected from alkyl, heteroalkyl, aryl, heteroaryl, aralkyl and heteroaralkyl.

$R^3$ and $R^4$ may both be hydrogen.

Where Z is $-NH_2$, i.e. $R^3$ and $R^4$ are both hydrogen, this group may be in a protected form. The protecting group may be selected from the group consisting of Fmoc, Boc, Ac, Bn and Z (or Cbz). Alternative protecting groups may be used, such as those described below in relation to protected forms.

Preferably, $R^5$ is hydrogen.

Preferably, Z is $-NH_2$, an amino acid or $-NR^5COR^6$. Where Z is $-NR^5COR^6$, preferably $R^5$ is hydrogen and $R^6$ is an aralkyl group substituted with a hydroxyl group, most preferably the aralkyl group is substituted on the alkyl portion of the group. $R^6$ may be $-CH(OH)Ph$ (i.e. Z is modified with a mandelyl group).

$R^9$ is preferably a group, optionally substituted, selected from alkyl, heteroalkyl, aryl, heteroaryl, aralkyl and heteroaralkyl.

The preferred compounds according to the first aspect of the invention present invention are the compounds listed below:

Compound I: Deoxy-Actagardine B N-[2-ethanolamine] monocarboxamide

Compound II: Deoxy-Actagardine B N-[4-butanolamine] monocarboxamide

Compound III: Actagardine N-[2-ethanolamine]monocarboxamide

Compound IV: Deoxy-actagardine B (3-amino-1,2-propanediol) monocarboxamide

Compound V: Deoxy-actagardine B (2-amino-1,3-propanol) monocarboxamide

Compound VI: Deoxy-actagardine B [tris(hydroxymethyl) methylamine]monocarboxamide Compound VII: Deoxy-actagardine B (1-amino-2-propanol) monocarboxamide Compound VIII: Deoxy-actagardine B (1-amino-3-propanol) monocarboxamide Compound IX: (L)-Phenylalanyl-(O)-deoxyactagardine B (ethanolamine) monocarboxamide Compound X: (L)-Tryptophanyl-(O)-deoxyactagardine B (ethanolamine) monocarboxamide Compound XI: (L)-Alanyl-(O)-deoxyactagardine B (ethanolamine) monocarboxamide Compound XII: (D)-Alanyl-(O)-deoxyactagardine B (ethanolamine) monocarboxamide Compound XIII: (L)-Isoleucinyl-(O)-deoxyactagardine B (ethanolamine) monocarboxamide Compound XIV: (L)-Leucinyl-(O)-deoxyactagardine B (ethanolamine) monocarboxamide Compound XV: N-Phenylacetyl deoxyactagardine B (ethanolamine) monocarboxamide Compound XVI: N-Acetyl deoxyactagardine B (ethanolamine) monocarboxamide Compound XVII: N-Mandelyl deoxyactagardine B (ethanolamine) monocarboxamide Compound XVIII: Deoxyactagardine B (N,N-bis(2-hydroxyethyl)ethylene diamine) monocarboxamide Additionally, or alternatively the preferred compounds according to the first aspect of the invention present invention may be selected from the compounds listed below:

Compound XX: Deoxy-Actagardine B N-[2-hydroxy-2-phenylethylamine]monocarboxamide Compound XXI: Deoxy-actagardine B (L-serine methyl ester) monocarboxamide Compound XXII: Deoxyactagardine B (N-(2-hydroxyethyl) ethylenediamine) monocarboxamide Compound XXIII: Deoxy-actagardine B (2-hydroxypiperazine) monocarboxamide Additionally, or alternatively the preferred compounds according to the first aspect of the invention present invention may be selected from the compounds listed below:

Compound XXX: (L)-Alanyl-(O)-deoxyactagardine B (ethanolamine) monocarboxamide

Compound XXXI: (D)-Alanyl-(O)-deoxyactagardine B (ethanolamine) monocarboxamide

Compound XXXII: (L)-Isoleucinyl-(O)-deoxyactagardine B (ethanolamine) monocarboxamide Compound XXXIII: (L)-Leucinyl-(O)-deoxyactagardine B (ethanolamine) monocarboxamide Compound XXXIV: N-Phenylacetyl deoxyactagardine B (ethanolamine) monocarboxamide Compound XXXV: N-Acetyl deoxyactagardine B (ethanolamine) monocarboxamide Compound XXXVI: N-Mandelyl deoxyactagardine B (ethanolamine) monocarboxamide The most preferred compounds are:
Compound I: Deoxy-Actagardine B N-[2-ethanolamine] monocarboxamide
Compound III: Actagardine N-[2-ethanolamine]monocarboxamide The most preferred compounds have improved antimicrobial activity in comparison to the actagardine and deoxyactagardine B compounds from which they are derived.

The present invention also provides variants, derivatives and precursors of the compounds of formula (I). These are described in detail below.

Variants

A variant of a compound of formula (I) includes a compound in which one or more, for example from 1 to 5, such as 1, 2, 3 or 4 amino acids are substituted by another amino acid. Preferably the amino acid is at a position selected from positions 2, 3, 4, 5, 8, 10, 11, 13, 15, 16 or 18 of the compound of formula (I).

Substitutions may be of one amino acid by another naturally occurring amino acid and may be conservative or non-conservative substitutions. Conservative substitutions include those set out in the following table, where amino acids on the same block in the second column and preferably in the same line in the third column may be substituted for each other:

| ALIPHATIC | Non-polar | G A |
| | | I L V |
| | Polar - uncharged | C S T M |
| | | N Q |
| | Polar - charged | D E |
| | | K R |
| AROMATIC | | H F W Y |

Alternatively, an amino acid may be substituted by one of the modified, non-natural or unusual amino acids described above.

A variant of a compound of the invention may include a compound where one or more crosslinks is a bridge other than a thionine bridge. Alternative bridges include, where appropriate, di-sulfide bridges, and amide and ester bridges (so-called macrolactam and macrolactone variants respectively).

Derivatives

Derivatives of compounds of the invention (including variants) are those in which one or more amino acid side chain of the compound of the invention has been modified, for example by esterification, amidation or oxidation.

Derivatives of compounds of the invention may be monoamide derivatives at one of the carboxy functions of actagardine. A derivative may include a compound in which the carboxy function of a side chain of an internal residue, e.g. that of the residue Glu11, is modified from —COOH to a group —COOR$^{10}$ in which R$^{10}$ represents hydrogen, ($C_1$-$C_4$) alkyl or ($C_1$-$C_4$)alkoxy ($C_2$-$C_4$)alkyl. Alternatively, the carboxy function of a side chain of an internal residue e.g. that of the residue Glu11, is modified from —COOH to a group —CONR$^1$R$^2$ where R$^1$ and R$^2$ are defined as above in relation to the C-terminus amide substituents.

Compound (I) is shown with crosslinks CROSSLINK 1-6, Lanthionine (Ser-Cys); CROSSLINK 7-12, Beta-methyl-lanthionine (Thr-Cys); and CROSSLINK 9-17, Beta-methyl-lanthionine (Thr-Cys). In one embodiment of the invention, one, two or three of these crosslinks may be thionine sulfoxide crosslinks.

Includes Other Forms

Included in the above compounds and polypeptide precursors are the well known ionic, salt, solvate, and protected forms. For example, a reference to carboxylic acid (—COON) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O-), a salt or solvate thereof, as well as conventional protected forms of a hydroxyl group.

For example, reference to the carboxylic acid-containing side chain of glutamic acid (Glu), which features as a residue in the compound of the invention, includes the carboxylate form. Where Z is —NH$_2$, reference to this group includes the protonated form of this amino group.

Isomers, Salts, Solvates, Protected Forms, and Prodrugs

Certain compounds may exist in one or more particular geometric, optical, enantiomeric, diasterioisomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

For example, the amino acid residues described herein may exist in any one of the particular stereoisomeric forms. Similarly, the R$^1$ and R$^2$ groups may exist in any one of the particular stereoisomeric forms, where such forms exist. Likewise, the groups R$^3$, R$^4$, R$^5$, R$^6$, R$^7$, R$^8$, R$^9$ and R$^{10}$ may exist in any one of the particular stereoisomeric forms, where such forms exist.

Where a compound or a precursor polypeptide of the invention includes a dihydroamino butyric acid residue, the residue may exist in either cis- or trans-forms.

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H(T); C may be in any isotopic form, including $^{12}$C $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in Berge, et al., "Pharmaceutically Acceptable Salts", *J. Pharm. Sci,* 66, 1-19 (1977).

For example, if the compound is anionic, or has a functional group which may be anionic (e.g., —COON may be —COO), then a salt may be formed with a suitable cation. Examples of suitable inorganic cations include, but are not limited to, alkali metal ions such as Na and K$^+$, alkaline earth cations such as Ca$^{2+}$ and Mg$^{2+}$, and other cations such as API. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999).

For example, an amine group may be protected as described previously where Z is —NH$_2$ above. Additionally, an amine group may be protected as an amide or a urethane, for example, as: a methyl amide (—NHC0—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as described previously in relation to the amino acid residues above. For example, a carboxylic acid group may be protected as an ester for example, as: a C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-Cl$_{1-7}$ alkyl ester (e.g. a benzyl ester; a nitrobenzyl ester); or as an amide, for example, as a methyl amide.

For example, a hydroxyl group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—COON) in the parent compound, with, where appropriate, prior protection of any other reactive groups present in the parent compound, followed by deprotection if required. Examples of such metabolically labile esters include, but are not limited to, those wherein R is C$_{1-20}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleaved by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Methods for Preparing Compounds of the Invention

The inventors have previously described methods for the preparation of lantibiotic compounds, as well as derivatives and variants, and precursors thereof. The inventors' co-pending earlier application PCT/GB2007/000138 (WO/2007/083112) is hereby incorporated by reference in its entirety. The compounds described in this document may be used as starting materials for the compounds described in the present invention.

Particular reference is made to the following sections in the inventors' co-pending application:
Expression Construct;
Recombinant Expression Vector;
Expression Cassettes;
Expression Libraries;
Host Cell including 'Lantibiotic-producing host cell' and 'Non-producer cell';
Production of Compounds of the Invention; and
Examples 1-4 and 7.

The compounds described herein may be used as starting materials for the synthesis of other compounds for use in the invention.

The actagardine compounds for use in the invention may be prepared from known actagardine compounds. Preferably, the actagardine compounds of the invention are prepared from actagardine, actagardine B and deoxyactagardine B. These antibiotics may be referred to as a 'parent lantibiotic' or a 'lantibiotic starting material'.

An actagardine compound may be produced by expression of a nucleic acid, for example in the form of an expression construct encoding a precursor polypeptide carried in a recombinant expression vector, in a host cell which carries an appropriate lantibiotic gene, such as the LanA gene, together with, where necessary, associated cluster genes required for conversion of a precursor polypeptide to an actagardine compound. Variant actagardine compounds may be produced by appropriate modification of the LanA gene using methods known per se in the art.

The LanO gene, which has been identified as part of the actagardine gene cluster, is thought to encode the protein responsible for the oxidation of the deoxy-form of actagardine compounds to actagardine in which Y is —S(O)—. Modification of this gene may allow the production of derivative compounds having an alternative crosslinked structure. Modification of the LanO gene also allows the relative levels of oxidized (Y=S(O)) and reduced (Y=S—) forms of the compounds produced in the host cell to be altered.

The LanM gene, which has also been identified as part of the actagardine gene cluster, is thought to encode the protein required for the conversion of a precursor polypeptide to a lantibiotic compound. Modulation of this gene, and other genes encoding modification proteins, may allow the production of derivative compounds having an alternative crosslinked structure. Modulation of these genes may also allow the production of compounds having or retaining an amino acid sequence attached to the N-terminus of the actagardine compound, such as a leader sequence.

Typically, those compounds produced by cell culture will have a free amine N-terminus (i.e. z is —NH$_2$) and a free carboxylic acid C-terminus (i.e. X is —OH). These termini may be derivatised as described in more detail below. Where an actagarine compound has a modified N-terminus, the starting material will typically have a free amine N-terminus. It will be appreciated that the compounds produced by cell culture may have a modified N-terminus. Thus, a compound for use as a starting material may include a compound where Z is —NHR$^3$, where R$^3$ is defined according to the compounds of formula (I).

Where the invention relates to the use of compounds derived from an actagardine compound starting material in which X1 and X2 represent Leu and Val respectively, the host cell may be A. liguriae NCIMB 41362 without any further modification.

Where host cells produce a mixture of starting material compounds, e.g. those in which Y is —S— or —S(O)—, the products may be isolated using standard separation techniques such as HPLC, e.g. as described in U.S. Pat. No. 6,022,851 for the production of Actagardine and Ala-Actagardine.

Following culture of the cell, the lantibiotic starting material may be recovered from the host cell culture unmodified. The recovered and modified compounds may be formulated in the form of a pharmaceutical composition, optionally in the form of a pharmaceutically acceptable salt.

Alternatively, the lantibiotic starting material, or the precursors, variants and derivatives thereof, may be obtained by chemical peptide synthesis, for example solid-phase peptide synthesis (SPPS). Such techniques are well known in the art. Preferably, the lantibiotic starting material is obtained from cell culture.

The compounds of the invention may be in substantially isolated form. Isolated compounds of the invention will be those as defined above in isolated form, free or substantially free of material with which it is associated such as polypeptides from which the compounds are derived. The compounds may of course be formulated with diluents or adjuvants and still for practical purposes be isolated.

A compound of the invention may also be in a substantially purified form, in which case it will generally comprise the compound in a preparation in which more than 90%, e.g. 95%, 98% or 99% of the compound in the preparation is a compound of the invention.

The compounds of the invention are prepared by reacting a lantibiotic starting material having a carboxyl C-terminus with a 2 to 6-fold molar excess of an appropriate amino alkyl or amino heteroalkyl group, in a suitable organic solvent such as dimethylformamide at a temperature typically between 0° C. and room temperature and in the presence of a suitable condensing agent. Representative examples of condensing agents are carbodiimide derivatives such as dicyclohexylcarbodiimide, phosphoazidates such as DPPA or benzotriazole-based coupling reagents such as PyBop™, HATU or TBTU.

Compounds of the invention where Z is an amino acid or —NR$^5$COR$^6$ may be prepared from a lantiobiotic starting material having an amino group N-terminus by means of a coupling reaction with an appropriate carboxylic acid in the presence of a condensing agent such as dicyclohexylcarbodiimide, phosphoazidates such as DPPA or benzotriazole-based coupling reagents such as PyBop™, HATU or TBTU. An organic amine base, such as triethylamine or diisopropylethylamine is generally added to expedite the reaction.

Alternatively, preformed activated derivatives of the appropriate acid, such as the pentafluorophenyl esters, may be used as reagents to react with the lantibiotic N-terminus. A catalyst, such as HOBt may be added to expedite the reaction. The solvent is typically DMF.

Where the carboxylic acid being coupled to the lantibiotic contains further functional groups that may interfere with the coupling reaction, suitable protection groups familiar to those skilled in the art may be employed. For example, Fmoc or tBoc protection groups may be employed for amino acid derivatives to be coupled to the N-terminus of the lantibiotic.

Compounds of the invention where Z is $-NR^3R^4$ may be prepared from a lantibiotic having an amino group N-terminus by means of a coupling reaction with an aldehyde or ketone in an organic solvent, such as dichloromethane, dimethylsulphoxide or acetic acid, in the presence of a suitable reducing agent, such as sodium borohydride or sodium triacetoxyborohydride. Such reducing agent may be used in solution or bound to a suitable resin, such as polystyrene. Depending on the reaction conditions, the aldehyde or ketone employed and the ratio of the reagents employed in the reaction, both mono- and di-alkylation of the N-terminus are possible. Alternatively, the reaction may be performed without a reducing agent. In which case it is possible to obtain compounds of the invention where Z is $-N=R^9$.

Compounds of the invention where Z is $-NR^5C(O)OR^6$; $-NR^5SOR^6$, $-NR^5SO_2R^6$; $-NR^5C(S)NR^6R^7$ or $-NR^5C(NR^8)NR^6R^7$ may be prepared from a lantiobiotic starting material having an amino group N-terminus by means of a coupling reaction with an appropriately activated substituent group reagent. Thus, compounds where Z is $-NR^5C(O)OR^6$, may be prepared using $ClC(O)OR^6$ and such like. Similarly, compounds where Z is $-NR^5SO_2R^6$ may be additional functionality that is protected with a protecting group. The protecting group may be removed after the coupling reaction as appropriate.

The compounds of the invention where Z is other than $-NH_2$ (i.e. compounds where $R^3$ and $R^4$ are not hydrogen) may be prepared from starting materials that are modified at either the C- or N-terminus. The other terminus may then be modified to provide the compounds of the invention. Thus, the sequence of substitutions can either feature N-terminal modification followed by C-terminal modification, or vice versa. Where issues of regioselectivity arise, for instance where the C-terminal substituent features an amino group, a suitable protection strategy may be employed.

Thus, a lantibiotic starting material where the N-terminus of the compound is an amino acid residue, $-NR^3R^4$, $-NR^5COR^6$, $-NR^5C(O)OR^6$; $-NR^5SOR^6$, $-NR^5SO_2R^6$, $-NR^5C(S)NR^6R^7$, $-NR^5C(NR^8)NR^6R^7$, or $-N=R^9$ (as defined previously in relation to the compounds of the invention), may equally be coupled with amino alcohols at the C-terminal.

The inventors have observed that under the coupling conditions used to couple an amino alcohol to the carboxyl C-terminus of a parent lantibiotic, the carboxyl group of a side chain amino acid residue, such as glutamic acid, may also be modified. Such compounds where both the C-terminus and a side chain of an amino acid are modified are also within the scope of the present invention. Appropriate manipulation of the reaction conditions may be used to modify the amount of product obtained where the side chain of an amino acid has been modified. Alternatively a protection and deprotection strategy may be employed to ensure that the side chain is not modified. Suitable amino acid residue side chain protecting groups are well known and include the protecting groups mentioned above.

Figure 3:
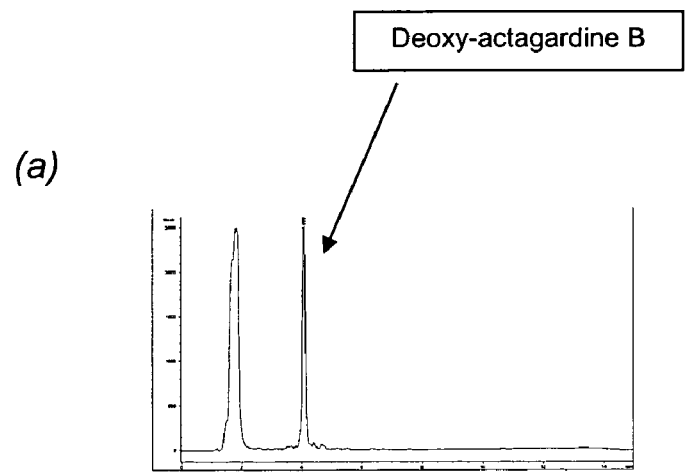
FIG. 3 shows the course of the reaction forming compound I as followed by analytical HPLC.
Figure 3:
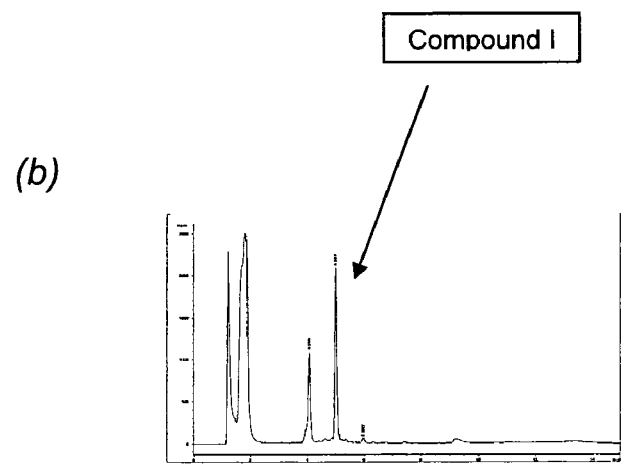
Figure 3:
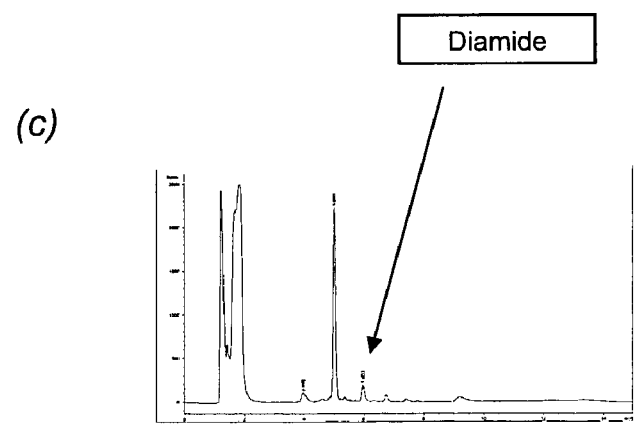

Reaction products may be identified by LC-MS. Reaction progression may be monitored by HPLC. See, for example, FIG. 3. HPLC may be used to monitor the consumption of the starting material, the appearance of the product and the production of side or decomposition products (if any).

The products and the starting material may be analysed by NMR spectroscopy. Such techniques have been described previously by the present inventors in PCT/GB2007/000138 (WO/2007/083112). The structure of the product lantiobiotic-based compound may be confirmed using standard techniques such as COSY, HMBC, TOCSY, HSQC and NOESY, as well as NOE techniques.

Pharmaceutically Acceptable Salt

A "pharmaceutically acceptable salt", may be an acid addition salt in which the base retains the biological effectiveness and properties of the compound and which is physiologically acceptable. Such salts include those formed with inorganic acids such as hydrochloric acid, hydrobromic acid, sulphuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Salts also include basic salts, such as an alkali or alkaline earth metal salt, e.g. a sodium, potassium, calcium or magnesium salt.

Additionally, or alternatively salts may be formed with any one of N-methyl-D-glutamine, L-arginine, L-tysine, choline, and tris(hydroxymethyl)aminomethane.

Pharmaceutical Compositions

The lantibiotic-based compounds of the present invention may be formulated together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilizers, solubilisers, surfactants (e.g., wetting agents), masking agents, colouring agents, flavouring agents, and sweetening agents. The formulation may further comprise other active agents, for example, other therapeutic or prophylactic agents. Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgement, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see "*Remington: The Science and Practice of Pharmacy*", 20th Edition, 2000, pub. Lippincott, Williams & Wilkins. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

For topical applications, the pharmaceutically acceptable compositions may be formulated in a suitable ointment or gel containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The percentage of active compound contained in such parental or topical compositions is highly dependent on the specific nature thereof, as well as the activity of the compound and the needs of the subject. However, percentages of active ingredient of 0.1% to 10% w/w employable, and will be higher if the composition is a solid which will be subsequently diluted to the above percentages. Preferably, the composition will comprise 0.2-2% w/w of the active agent in solution.

Further teaching regarding suitable carriers, adjuvants, excipients, etc. can be found in standard pharmaceutical texts, for example, "*Remington: The Science and Practice of Pharmacy*", 20th Edition, 2000, pub. Lippincott, Williams & Wilkins; and Handbook of Pharmaceutical Excipients, 2nd edition, 1994.

Administration of Compounds

Lantibiotic-based compounds and compositions of the invention may be administered to a subject in a method of medical treatment or prophylaxis. The subject may be a human or animal subject. The animal subject may be a mammal, or other vertebrate.

Thus there is provided a compound of the invention for use in a method of treatment or prophylaxis of a subject. There is also provided use of a compound of the invention for the manufacture of a medicament for use in a method of treatment or prophylaxis of a subject.

Particularly, the compounds of the invention may be used to treat a microbial, typically a bacterial, infection in a subject The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The infection may be an infection of the gastrointestinal tract, preferably the intestine, and most preferably of the colon. Particularly, in one aspect of the present invention, there is provided a method of treating a bacterial infection. Preferably, the infection is a *Clostridium* infection, preferably a *Clostridium perfringens*, Clostridium difficile, Clostridium tetani or *Clostridium botulinum* infection, most preferably *C. difficile* infection. These methods provide new and useful alternatives to the method of treatment utilising a type-A lantibiotic, vancomycin or metronidazole.

The bacterial infection may be an *Enterococcus* sp, *Streptococcus* spp, *Staphylococcus* spp. or *Clostridium difficile* infection.

The invention also provides a method for treating of a disease caused by a bacterial infection of the intestine, and preferably the colon. The method may be used to treat pseudomembranous colitis or *Clostridium difficile*-associated diarrhoea (CDAD). Preferably, the infection is a *Clostridium* infection, preferably a *Clostridium perfringens, Clostridium difficile, Clostridium tetani* or *Clostridium botulinum* infection, most preferably *C. difficile* infection.

The present invention also provides a method of treatment or prophylaxis of a subject comprising the step of administering a compound or composition of the invention to the subject. Preferably the compound or composition is administered orally.

The present invention also relates to the treatment or prophylaxis of a *Clostridium difficile, Helicobacter pylori* or vancomycin-resistant enterococci (VRE) infection. Preferably the invention relates to a *Clostridium difficile* infection.

The present invention also relates to the treatment of an infection that has not been eradicated by treatment with another active compound, preferably a compound that is not a type-B lantibiotic. The other active compound may be vancomycin.

Where compound of the present invention is administered to a subject having an infection that has not been eradicated by treatment with another active compound, the type-B lantibiotic may be administered within 1 day, 1 week or 1 month of the last administration of the other active compound.

The compounds and compositions may also be used for systemic treatment of bacteraemia (including catheter related bacteraemia), pneumonia, skin and skin structure infections (including surgical site infections), endocarditis and osteomyelitis. These and other such treatments may be directed against causative agents such as staphylococci, streptococci, enterococci. The compounds of the invention or compositions thereof may also be used for topical treatment of skin infections including acne i.e. *Propionibacterium acnes*. The compounds and compositions thereof may also be used in the treatment of eye infections, such as conjunctivitis.

The compounds may also be used in the treatment or prevention of infection of the skin in wounds or burns. In addition, the compounds and compositions described herein for use in the invention may be used in prophylactic methods. This may be practiced on subjects at risk of infection (e.g. patients entering a hospital) or on health professionals or other carers at risk of being carriers of such infections.

Most preferably, the compounds and compositions may be used for treatment of gut super-infection, such as that caused by *Clostridium difficile* including multiply-resistant *C. difficile* (pseudomembranous colitis). The compound or composition may be administered orally. Gut infections associated with *Helicobacter pylori* may also be treated.

The present invention also provides a method for treating CDAD. Complete relief of symptoms of CDAD by the end of the treatment may be defined as resolution to less than 3 bowel movements per day (whether formed or unformed), and no associated fever, elevated WBC (white blood cell) count, or abdominal pain.

The method of treatment may be of a bacterial infection, including a skin, mucosal, enteric or systemic infection.

The compounds according to the invention can be administered enterally (orally), parenterally (intramuscularly or intravenously), rectally, vaginally, or locally (topically). They can be administered in the form of solutions, powders (tablets, capsules including microcapsules), ointments (creams or gel), or suppositories. Possible auxiliaries for formulations of this type-Are the pharmaceutically customary liquid or solid fillers and extenders, solvents, emulsifiers, lubricants, flavor corrigents, colorants and/or buffer substances.

As an expedient dose, 0.1-1,000, preferably 0.2-100, mg/kg of body weight are administered. They are expediently administered in dose units which contain at least the efficacious daily amount of the compounds according to the invention, e.g. 30-3,000, preferably 50-1,000, mg. Preferably, the effective amount of the compound to be administered is from around 100 to around 2,000 mg per patient per day.

The experimental basis of the present invention, including its best mode, will now be further described in detail, by way of example only, with reference to the accompanying drawings.

Synthesis of Lantiobiotic-Based Compounds

The following compounds were made, in which the parent lantibiotic, and the groups X1, X2, Z, and $R^1$ and $R^2$ were as follows:

| Compound | Lantibiotic | X1 | X2 | Y | Z | $R^1$ | $R^2$ |
|---|---|---|---|---|---|---|---|
| I | Deoxy-actagardine B | Leu | Val | —S— | —NH$_2$ | 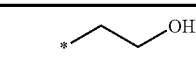 | H |
| II | Deoxy-actagardine B | Leu | Val | —S— | —NH$_2$ | 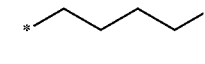 | H |
| III | Actagardine | Val | Ile | —S(O)— | —NH$_2$ | 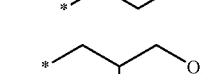 | H |
| IV | Deoxy-actagardine B | Leu | Val | —S— | —NH$_2$ | 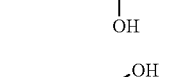 | H |
| V | Deoxy-actagardine B | Leu | Val | —S— | —NH$_2$ | 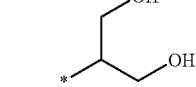 | H |
| VI | Deoxy-actagardine B | Leu | Val | —S— | —NH$_2$ | 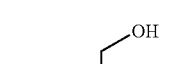 | H |

-continued

| Compound | Lantibiotic | X1 | X2 | Y | Z | R¹ | R² |
|---|---|---|---|---|---|---|---|
| VII | Deoxy-actagardine B | Leu | Val | —S— | —NH$_2$ | *-CH$_2$-CH(OH)-CH$_3$ | H |
| VIII | Deoxy-actagardine B | Leu | Val | —S— | —NH$_2$ | *-CH$_2$CH$_2$CH$_2$OH | H |
| XVIII | Deoxy-actagardine B | Leu | Val | —S— | —NH$_2$ | *-CH$_2$CH$_2$-N(CH$_2$CH$_2$OH)$_2$ | H |
| IX | Deoxy-actagardine B | Leu | Val | —S— | -Phe | *-CH$_2$CH$_2$OH | H |
| X | Deoxy-actagardine B | Leu | Val | —S— | -Tyr | *-CH$_2$CH$_2$OH | H |

The asterisk indicates the point where R¹ is attached to the nitrogen atom that is linked to alanine residue at position 19 via an amide bond.

The following compounds were also made, in which the parent lantibiotic, and the groups X1, X2, Z, and R¹ and R² were as follows:

| Compound | Lantibiotic | X1 | X2 | Y | Z | R¹ | R² |
|---|---|---|---|---|---|---|---|
| XX | Deoxy-actagardine B | Leu | Val | —S— | —NH$_2$ | *-CH$_2$-CH(OH)-Ph | H |
| XXI | Deoxy-actagardine B | Leu | Val | —S— | —NH$_2$ | *-CH(CH$_2$OH)-C(O)-OCH$_3$ | H |
| XXII | Deoxy-actagardine B | Leu | Val | —S— | —NH$_2$ | *-CH$_2$CH$_2$-NH-CH$_2$CH$_2$OH | H |
| XXIII | Deoxy-actagardine B | Leu | Val | —S— | —NH$_2$ | *-N(2-hydroxypiperidinyl) | H |

Preparation of Compounds I-VIII, XVIII, and XX-XXIII
General Procedure 1

To a solution of lantiobiotic (e.g. actagardine, actagardine B, or deoxy-actagardine B) (200 mg, 108 nmol), an appropriate aminoalcohol (330 nmol) and diisopropylethylamine (410 nmol) in dry dimethylformamide (2 ml) was added portion-wise a solution of benzotriazole-1-yl-oxy-tris-pyrrolidino-phosphonium hexafluorophosphate (PyBop™) (125 mg, 258 nmol) in dry dimethylformamide (1.5 ml). The mixture was analysed by HPLC to follow the progress of the reaction, adding further aliquots of the PyBop™ solution until all the starting material had been consumed. HPLC analysis at this stage also showed variable amounts (5-20%) of the diamide (see FIG. 3). After completion of the reaction, the mixture was diluted with 30% acetonitrile in 20 mM Kpi aqueous phosphate buffer, pH7 (10 ml) and the monoamide was purified by preparative HPLC using the conditions described in Table 1 The appropriate fractions were concentrated to 25% of their original volume and desalted by loading on to a preconditioned C18 Bond Elut column (500 mg) which was subsequently washed by sequential elution with two column volumes of 30, 40, 70 and 90% aqueous methanol. Evaporation of the appropriate fractions gave the desired products as white solids. Samples were analysed by LC-MS using the conditions described below.

TABLE 1

Preparative HPLC conditions for the separation of lantiobiotic (e.g. actagardine, actagardine B, or deoxy-actagardine B) and aminoalcohol derivatised product.

| | |
|---|---|
| Column | Capitol HPLC Ltd C18 - BDS - HL5 - 26052 15 cm × 20 mm |
| Solvent A | 30% Acetonitrile in 20 mM Potassium Phosphate pH 7.0 |
| Solvent B | 65% Acetonitrile in 20 mM Potassium Phosphate pH 7.0 |
| Detection | 268 nm |
| Flow Rate | 10 ml/min |
| Time (T) = 0 min | 100% A |
| T = 1 min | 100% A |
| T = 19 min | 25% B |
| T = 20 min | 100% B |
| T = 25 min | 100% B |
| T = 26 min | 100% A |
| T = 30 min | 100% A |
| Collection | Start 8 min; End 20 min; 1 minute fractions |

Compound I: Deoxy-Actagardine B N-[2-ethanolamine]monocarboxamide

Was obtained from coupling of deoxyactagardine B and ethanolamine according to General Procedure 1. Yield 18 mg, 85% yield. [M+2H $2^+$] calculated 979.0. found 980.2.

Compound II: Deoxy-Actagardine B N-[4-butanolamine]monocarboxamide

Was obtained from coupling of deoxyactagardine B and butanolamine according to General Procedure 1. Yield 9 mg, 43% yield. [M+2H $2^+$] calculated 972.50. found 979.9.2

Compound III: Actagardine N-[2-ethanolamine]monocarboxamide

Was obtained from coupling of deoxyactagardine B and ethanolamine according to General Procedure 1. Yield 11 mg, 53% yield. [M+2H $2^+$] calculated 966.5. found 966.1

Compound IV: Deoxy-Actagardine B (3-amino-1,2-propanediol) monocarboxamide

Was obtained from coupling of deoxyactagardine B and 3-amino-1,2-propanediol according to General Procedure 1. Yield 18 mg, 87% yield. [M+2H $2^+$] calculated 973.5.0. found 973.9

Compound V: Deoxy-Actagardine B (2-amino-1,3-propanol) monocarboxamide

Was obtained from coupling of deoxyactagardine B and 2-amino-1,3-propanol according to General Procedure 1. Yield 20 mg, 96% yield. [M+2H $2^+$] calculated 973.5. found 973.9

Compound VI: Deoxy-Actagardine B [tris(hydroxymethyl)methylamine]monocarboxamide Was obtained from coupling of deoxyactagardine B and tris(hydroxymethyl)methylamine according to General Procedure 1. Yield 13 mg, 69% yield. [M+2H $2^+$] calculated 988.5. found 988.6

Compound VII: Deoxy-Actagardine B (1-amino-2-propanol) monocarboxamide

Was obtained from coupling of deoxyactagardine B and 1-amino-2-propanol according to General Procedure 1. Yield 16 mg, 78% yield. [M+2H $2^+$] calculated 965.5. found 965.6

Compound VIII: Deoxy-Actagardine B (1-amino-3-propanol) monocarboxamide

Was obtained from coupling of deoxyactagardine B and 1-amino-3-propanol according to General Procedure 1. Yield 19 mg, 87% yield. [M+2H $2^+$] calculated 965.5. found 965.3

Compound XVIII: Deoxyactagardine B (N,N-bis(2-hydroxyethyl)ethylene diamine) monocarboxamide Was obtained from coupling of deoxyactagardine B and N,N-bis(2-hydroxyethyl)ethylene diamine according to General Procedure 1. Yield 48%. [M+2H $2^+$] calculated 1002.0. found 1002.3

Compound XX: Deoxy-Actagardine B N-[2-hydroxy-2-phenylethylamine]monocarboxamide Was obtained from coupling of deoxyactagardine B and N-[2-hydroxy-2-phenylethylamine] according to General Procedure 1. [M+2H $2^+$] calculated 995.5. found 995.8.

Compound XXI: Deoxy-actagardine B (L-serine methyl ester) monocarboxamide

Was obtained from coupling of deoxyactagardine B and L-serine methyl ester according to General Procedure 1. [M+2H $2^+$] calculated 987.5. found 986.9.

Compound XXII: Deoxyactagardine B (N-(2-hydroxyethyl)ethylenediamine) monocarboxamide Was obtained from coupling of deoxyactagardine B and N-(2-hydroxyethyl)ethylenediamine according to General Procedure 1. [M+2H $2^+$] calculated 980. found 979.8.

Compound XXIII: Deoxy-actagardine B (2-hydroxypiperazine) monocarboxamide

Was obtained from coupling of deoxyactagardine B and 2-hydroxypiperazine according to General Procedure 1. [M+2H $2^+$] calculated 978.5. found 977.7.

Preparation of Compounds IX and X

General Procedure 2 exemplified for (L)-Tryptophanyl-(O)-deoxyactagardine B N-(9-Fluorenylmethoxycarbonyl)-tryptophan-O-pentafluorophenyl ester (80 mg, 135 nmol) was added to a solution of 1-hydroxybezotriazole hydrate (18 mg, 135 nm) in dry dimethylformamide (1 ml). The mixture was then added to a solution of deoxyactagardine B (50 mg, 27 nmol) in dry dimethylformamide (0.5 ml). The mixture was left at room temperature for 15 min, after which all the starting material had been consumed. Water (0.05 ml) and piperidine (0.1 ml) were added and the mixture was left at room temperature for 1 h. The reaction mixture was diluted into 30% aqueous methanol and the resulting white suspension loaded on to a 1 g C18 solid phase extraction cartridge. Material was eluted with fractions of 40%, 50%, 60% and 70% aqueous methanol. The 60% fraction was evaporated to dryness, leaving a tan solid. Yield=35 mg (63%) [M+2H$^{2+}$] calculated 1030.0. found 1030.1

Compound X:
(L)-Tryptophanyl-(O)-deoxyactagardine B (ethanolamine) monocarboxamide Was obtained from coupling of (L)-Tryptophanyl-(O)-deoxyactagardine B (50 mg) and ethanolamine according to General Procedure 1. Yield 23 mg, 45% yield. [M+2H 2$^{2+}$] calculated 1051.5. found 1051.8

(L)-Phenylalanyl-(O)-deoxyactagardine B

Was obtained from the coupling of deoxyactagardine B and N-(9-Fluorenylmethoxycarbonyl)-phenylalanine-O-pentafluorophenyl ester according to General Procedure 2. Yield 65% yield. [M+2H$^{2+}$] calculated 1010.5. found 1011.0

Compound IX:
(L)-Phenylalanyl-(O)-deoxyactagardine B (ethanolamine) monocarboxamide Was obtained from coupling of (L)-Phenylalanyl-(O)-deoxyactagardine B (50 mg) and ethanolamine according to General Procedure 1. Yield 23 mg, 45% yield. [M+2H$^{2+}$] calculated 1032.0. found 1032.2

Compounds XI-XVIII and XXX-XXXVI may be prepared in a similar manner to the methods which are described above.

High Performance Liquid Chromatography

HPLC analyses were performed using a Hewlett Packard 1050 series HPLC system with the parameters as described below:

Column: Zorbax SB-C18, 4.6×150 mm, 5µ
Mobile Phase A: 30% Acetonitrile in 20 mM potassium phosphate buffer pH 7.0
Mobile Phase B: 65% Acetonitrile in 20 mM potassium phosphate buffer pH 7.0
Flow rate: 1 ml/min
Gradient:

| Time 0 min | 100% | A | 0% | B |
| Time 10 min | 0% | A | 100% | B |
| Time 11 min | 0% | A | 100% | B |
| Time 11.2 min | 100% | A | 0% | B |
| Cycle time 15 min | | | | |

Injection volume: 10 µl
Detection: 210 nm
High performance liquid chromatography-mass spectrometry (HPLC-MS)

HPLC-MS analyses were performed on a Hewlett Packard™ 1050 series HPLC system linked to a Micromass™ Platform LC (operated with MassLynx™ version 3.5 software) with the following parameters:
Column: Agilent Zorbax™ SB-C18 150×4.6 mm 5µ
Flow rate: 1 ml/min
Mobile phase: A 10% acetonitrile, 0.1% formic acid 90% water.
    B 90% acetonitrile, 0.1% formic acid, 90% water.
    Linear gradient A to B over 10 minutes, hold 1 min, B-A
Wavelength: 200-400 nm
Injection volume: 10 µl
Post column split: 1:10
Mass spectrometer: Micromass™ Platform LC
Mode: Electrospray positive
Nitrogen flow: 380 l/hr
Capillary voltage: 40V
Skimmer lens offset: 5V

Example 1

Solubility of Alcoholamine Derivatives

Typically, compounds of the invention were isolated using phosphate buffers. The water solubility of deoxyactagardine B was measured at 4.5 g/l, whereas the aqueous solubility of the corresponding ethanolamide derivative Compound I was measured at 15 g/l.

Example 2

Antibacterial Activity of Alcoholamine Derivatives

The compounds of the invention show antimicrobial activity in vitro and in vivo. They are most active against *Enterococci* spp, *Streptococci* spp and *Clostridium difficile* (Tables 2-4A) and some derivatives have improved activity compared to the parent lantibiotic.

Susceptibility testing for all aerobic organisms with the exception of *Streptococcus pneumoniae* was performed by two-fold serial antibiotic dilutions in Mueller-Hinton Broth supplemented with 50 µg/ml Ca$^{2+}$ unless otherwise noted. Susceptibility testing for *S. pneumoniae* was performed by two-fold serial antibiotic dilutions in Brain-Heart-Infusion Broth supplemented with 50 µg/ml Ca$^{2+}$ unless otherwise noted. Actively growing broth cultures were diluted to contain $10^5$ to $10^6$CFU/ml by adjusting to an OD600 of 0.2-0.3. They were then diluted a further 1:100 in fresh sterile broth. The assays were performed in duplicate in sterile 96-well microtitre plates in a total volume of 200 µl (160 µl broth, 20 µl antimicrobial agent, 20 µl inoculum) in a concentration range from 64 µg/ml to 0.06 µg/ml. Plates were incubated aerobically, with shaking, for 18-20 hours at 37° C. with the minimum inhibitory concentration (MIC) defined as the lowest concentration of drug that prevented visible growth. Clinical isolates of *Clostridium difficile* were tested in Wilkins-Chalgren Anaerobe Agar under anaerobic conditions. In all cases, vancomycin was used as a reference antibiotic

TABLE 2

MIC data (µg/ml) for actagardine, deoxy-actagardine B, vancomycin and compounds I-VIII against a panel of common pathogens:

| | | | Compound | | | | | | | | |
|---|---|---|---|---|---|---|---|---|---|---|---|
| Micro organism | Acta. | Deoxyacta. B | I | II | III | IV | V | VI | VII | VIII | Vanc. |
| *E. faecium* 7131121 | >64 | 64 | 8 | >64 | 64 | >64 | >64 | 64 | >64 | >64 | >64 |

TABLE 2-continued

MIC data (μg/ml) for actagardine, deoxy-actagardine B, vancomycin and compounds I-VIII against a panel of common pathogens:

| Micro organism | Compound | | | | | | | | | | |
|---|---|---|---|---|---|---|---|---|---|---|---|
| | Acta. | Deoxyacta. B | I | II | III | IV | V | VI | VII | VIII | Vanc. |
| E. faecium 19579 | 16 | 32 | 16 | 32 | 16 | 16 | 16 | 16 | 16 | 16 | 4 |
| E. faecalis 29212 | 4 | 32 | 4 | 8 | 4 | 32 | 32 | 32 | 8 | 16 | 4 |
| S. aureus R33 | 32 | 8 | 4 | 8 | 16 | 32 | 32 | 32 | 32 | 32 | 1 |
| S. aureus SH1000 | 16 | 32 | 4 | 8 | 8 | 16 | 16 | 16 | 16 | 32 | 2 |
| S. epidermis 11047 | 32 | 16 | 8 | 8 | 32 | 64 | 64 | 64 | 64 | 64 | 2 |
| M. luteus 4698 | 1 | 1 | 0.25 | 8 | 1 | 8 | 16 | 16 | 16 | 32 | 2 |
| S. pneumoniae R6 | 4 | 4 | 2 | 8 | 4 | 16 | 16 | 16 | 64 | 64 | >64 |

In the table above, Acta. refers to actagardine, Deoxyacta. B refers to deoxyactagardine-B, and Vanc. refers to vancomycin.

TABLE 3

MIC data (μg/ml) for actagardine, deoxy-actagardine B and compounds I and II against a panel of *Staphyloccus*, *enterococci* and *streptococci*.

| | Actagardine | Deoxyacta-gardine-B | I | III |
|---|---|---|---|---|
| Vancomycin intermediate *Staphyloccus aureus* | | | | |
| S. aureus V99 | 32 | 32 | 32 | 16 |
| S. aureus MI | >32 | >32 | 32 | 32 |
| S. aureus Mu3 | 32 | 32 | 32 | 32 |
| S. aureus 26 | 32 | 32 | >32 | 32 |
| S. aureus Mu50 | 32 | 32 | >32 | 32 |
| S. aureus 2 | 32 | 32 | 32 | 32 |
| S. aureus NJ | >32 | >32 | >32 | >32 |
| Methicillin resistant *Staphyloccus aureus* | | | | |
| S. aureus 12232 | 16 | 16 | 32 | 8 |
| S. aureus R36 | 16 | 16 | 16 | 16 |
| S. aureus R34 | 16 | 16 | 16 | 8 |
| S. aureus R39 | 32 | 32, | >32 | >32 |
| S. aureus R40 | 32 | 32 | 32 | 32 |
| S. aureus W71 | 32 | 32 | >32 | 32 |
| S. aureus W74 | 32 | 32 | 32 | 32 |
| S. aureus W96 | 32 | 32 | >32, | >32 |
| S. aureus W97 | 32 | 32 | >32 | >32 |
| S. aureus W98 | 16 | 16 | 32 | 32 |
| S. aureus W99 | >32 | >32 | 32 | 32 |
| Methicillin sensitive *Staphyloccus aureus* | | | | |
| S. aureus G15 | >32 | >32 | >32 | >32 |
| S. aureus G20 | 32 | 32 | >32 | 32 |
| S. aureus G22 | 32 | 32 | >32 | 32 |
| S. aureus G23 | 32 | 32 | >32 | 32 |
| S. aureus G28 | 16 | 16 | 32 | 16 |
| S. aureus G30 | 32 | 32 | >32 | 32 |
| S. aureus G31 | >32 | >32 | >32 | >32 |
| S. aureus G32 | 32 | 32 | >32 | 32 |
| S. aureus G33 | 32 | 32 | >32 | 32 |
| S. aureus G35 | 32 | 32 | >32 | >32 |
| S. aureus SH1000 | 16 | 16 | 32 | 16 |

TABLE 3-continued

MIC data (μg/ml) for actagardine, deoxy-actagardine B and compounds I and II against a panel of *Staphyloccus*, *enterococci* and *streptococci*.

| | Actagardine | Deoxyacta-gardine-B | I | III |
|---|---|---|---|---|
| Methicillin sensitive *Staphylococcus epidermidis* | | | | |
| S. epidermidis GRL05001 | >32 | >32 | >32 | >32 |
| S. epidermidis GRL05002 | >32 | >32 | >32 | >32 |
| S. epidermidis GRL05003 | 32 | 32 | >32 | 32 |
| S. epidermidis GRL05004 | >32 | >32 | >32 | 32 |
| S. epidermidis GRL05005 | >32 | >32 | >32 | >32 |
| S. epidermidis GRL05006 | >32 | >32 | >32 | >32 |
| S. epidermidis GRL05007 | >32 | 32 | >32 | >32 |
| S. epidermidis GRL05008 | >32 | >32 | >32 | >32 |
| S. epidermidis GRL05009 | >32 | >32 | >32 | >32 |
| S. epidermidis GRL05010 | >32 | >32 | >32 | >32 |
| Methicillin resistant *Staphylococcus epidermidis* | | | | |
| S. epidermidis 7755298 | >32 | >32 | >32 | >32 |
| S. epidermidis 7865688 | >32 | >32 | >32 | >32 |
| S. epidermidis 7753921 | >32 | >32 | >32 | >32 |
| S. epidermidis GRL05011 | >32 | >32 | >32 | >32 |
| S. epidermidis GRL05013 | >32 | >32 | >32 | >32 |
| S. epidermidis GRL05014 | >32 | >32 | >32 | >32 |
| S. epidermidis GRL05015 | >32 | >32 | >32 | >32 |
| S. epidermidis GRL05017 | >32 | >32 | >32 | >32 |
| S. epidermidis GRL05019 | >32 | >32 | >32 | >32 |
| S. epidermidis GRL05020 | 32 | 32 | 32 | 32 |

TABLE 3-continued

MIC data (μg/ml) for actagardine, deoxy-actagardine B and compounds I and II against a panel of *Staphyloccus*, *enterococci* and *streptococci*.

| | Actagardine | Deoxyacta-gardine-B | I | III |
|---|---|---|---|---|
| Vancomycin sensitive enterococci | | | | |
| E. faecalis 7754422 | 32 | 32 | 8 | 8 |
| E. faecium 7865229 | >32 | >32 | >32 | >32 |
| E. faecium 19579 | 16 | 16 | 32 | 16 |
| E. faecalis GRL05022 | 16 | 16 | 16 | ,8 |
| E. faecalis GRL05023 | 8 | 8 | 8 | 8 |
| E. faecalis GRL05024 | 16 | 16 | 8 | 8 |
| E. faecalis GRL05026 | 16 | 16 | 16 | 8 |
| E. faecalis GRL05027 | 8 | 8 | 16 | 8 |
| E. faecalis GRL05029 | 8 | 8 | 16 | 4 |
| E. faecalis GRL05030 | 8 | 8 | 8 | 4 |
| Vancomycin resistant enterococci | | | | |
| E. faecium 7662769 | >32 | >32 | >32 | >32 |
| E. faecium 7634337 | >32 | >32 | >32 | >32 |
| E. faecium 7865532 | >32 | >32 | >32 | >32 |
| E. faecium 9709024 | >32 | >32 | >32 | >32 |
| E. faecium GRL05031 | 4 | 4 | 4 | 4 |
| E. faecium GRL05032 | 4 | 4 | 4 | 4 |
| E. faecium 9710577 | >32 | >32 | >32 | >32 |
| E. faecium GRL05033 | 8 | 8 | 8 | 8, 4 |
| E. faecium GRL05034 | 32, 16 | 32, 16 | >32 | 16 |
| E. faecium GRL05035 | 32, 16 | 32, 16 | >32 | 16 |

TABLE 3-continued

MIC data (μg/ml) for actagardine, deoxy-actagardine B and compounds I and II against a panel of *Staphyloccus*, *enterococci* and *streptococci*.

| | Actagardine | Deoxyacta-gardine-B | I | III |
|---|---|---|---|---|
| Streptococcus pyogenes | | | | |
| S. pyogenes 7755441 | ≤0.5 | ≤0.5 | ≤0.5 | ≤0.5 |
| S. pyogenes 7713283 | 1 | ≤0.5 | 1 | ≤0.5 |
| S. pyogenes 7865844 | ≤0.5 | ≤0.5 | ≤0.5 | ≤0.5 |
| S. pyogenes 7755255 | ≤0.5 | ≤0.5 | ≤0.5 | ≤0.5 |
| S. pyogenes 7755584 | ≤0.5 | ≤0.5 | 1 | ≤0.5 |
| S. pyogenes GRL05045 | ≤0.5 | ≤0.5 | 1 | ≤0.5 |
| S. pyogenes 7865253 | ≤0.5 | ≤0.5 | ≤0.5 | ≤0.5 |
| S. pyogenes 7865289 | ≤0.5 | ≤0.5 | 1 | ≤0.5 |
| S. pyogenes GRL05041 | ≤0.5 | ≤0.5 | 1 | ≤0.5 |
| S. pyogenes GRL05042 | ≤0.5 | ≤0.5 | ≤0.5 | ≤0.5 |
| Viridans streptococci | | | | |
| S. mitis 1 7722543 | 8 | 8 | 8 | 4 |
| S. oralis 7862912.1 | 8 | 8 | 32 | 8 |
| S. mitis 1 7863547 | 4 | 4 | 4 | 4 |
| S. salivarius GRL05064 | 2 | 2 | 1 | 1 |
| S. constellatus GRL05065 | >32 | >32 | >32 | >32 |
| S. mitis GRL05062 | 8 | 8 | 16 | 8 |
| S. mitis GRL05067 | 16 | 16 | 8 | 16 |
| S. acidominimus 7862865 | 4 | 4 | 4 | 4 |

TABLE 4

MIC data (μg/ml) for actagardine, deoxy-actagardine B, vancomycin and compounds I-VIII against *Clostridium difficile*

| Clostridium difficile | Acta. | Deoxyacta. B | I | II | III | IV | V | VI | VII | VIII | Vanc. |
|---|---|---|---|---|---|---|---|---|---|---|---|
| C. difficile 37779 | 4 | 4 | 2 | — | 2 | 2 | — | — | 2 | 2 | 1 |
| C. difficile 19126 | 4 | 4 | 2 | — | 2 | 2 | 4 | 4 | 4 | 2 | 1 |
| C. difficile B32 | 4 | 4 | 2 | — | 2 | — | — | — | — | — | 1 |
| C. difficile E16 | 4 | 4 | 2 | — | 2 | — | — | — | — | — | 1 |
| C. difficile E4 | 2 | 4 | 1 | — | 1 | — | — | — | — | — | 1 |
| C. difficile P24 | 4 | 4 | 1 | — | 2 | — | — | — | — | — | 1 |
| C. difficile 027C | 1 | 4 | 0.5 | — | 1 | — | — | — | — | — | 0.5 |
| C. difficile 027SM | 2 | 4 | 0.5 | — | 1 | — | — | — | — | — | 0.5 |
| C. difficile P49 | 2 | 4 | 1 | — | 1 | — | — | — | — | — | 0.5 |
| C. difficile P59 | 2 | 4 | 2 | — | 1 | — | — | — | — | — | 1 |
| C. difficile P62 | 2 | 4 | 0.5 | — | 1 | — | — | — | — | — | 0.5 |
| C. difficile E101 | 4 | 4 | 2 | — | 2 | — | — | — | — | — | 1 |

In the table above, Acta. refers to actagardine, Deoxyacta. B refers to deoxyactagardine-B, and Vanc. refers to vancomycin.

In addition, compounds XX-XXIII were tested against *Clostridium difficile*, and the MIC data is given below.

TABLE 4A

Activity of Type-B lantibiotics Against *C. difficile*

| *Clostridium difficile* | L | LI | LII | LIII |
|---|---|---|---|---|
| *C. difficile* 19126 | 2 | 4 | 2 | 4 |
| *C. difficile* 37779 | 2 | 4 | 2 | 4 |
| *C. difficile* 027C | 2 | 2 | 2 | 4 |
| *C. difficile* 630 | 2 | 4 | 2 | 2 |

Example 3

Figure 2:
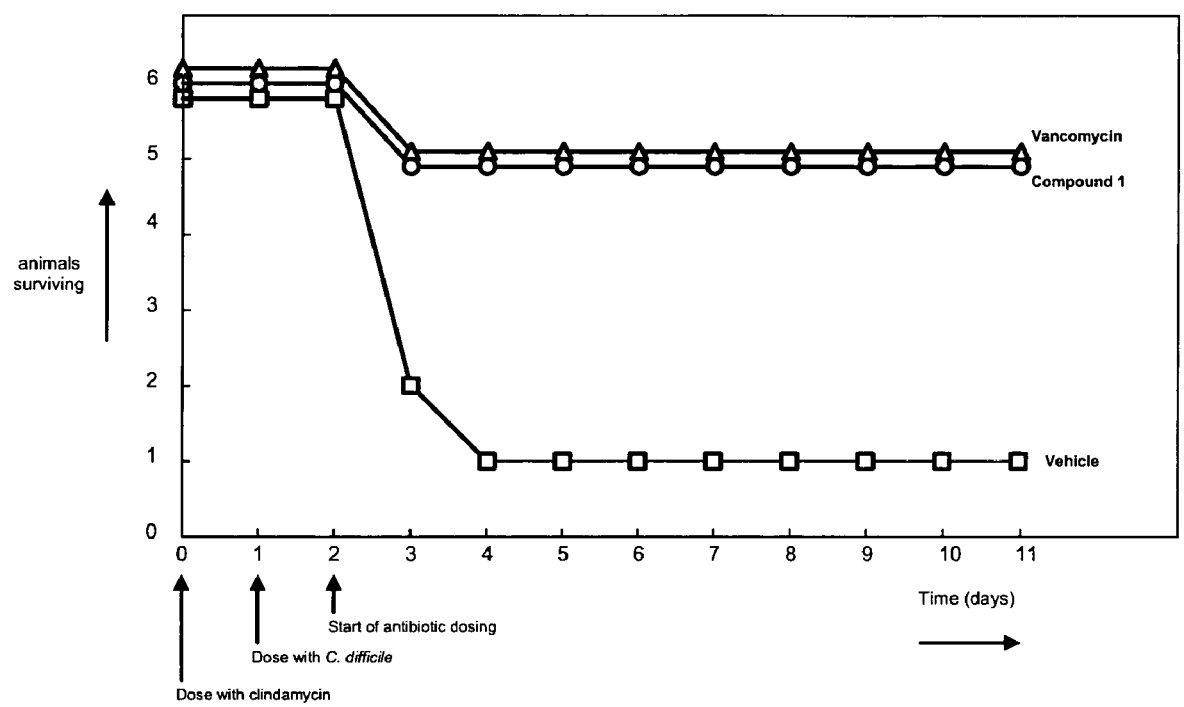
FIG. 2 shows the efficacy in vivo of compound I in the hamster model of *C. difficile*-associated cecitis.

In Vivo Efficacy of Type-B Antibiotics in the Hamster Model of *C. difficile* Associated Cecitis The in vivo efficacy of two of the compounds of the invention (compounds I and III) in the treatment of *C. difficile* infections was evaluated in the standard animal model for CDAD, clindamycin induced cecitis in the hamster. The results are summarised in FIGS. 1 and 2.

In the first experiment (FIG. 1) groups of 6 animals were dosed with approximately $10^7$ cells of *C. difficile* strain VPI 10463 and 24 hours later with a subcutaneous dose of 10 mg/kg clindamycin phosphate. After a further 24 h, the groups were then treated either with vehicle, vancomycin or compound III three times daily at 50 mg/kg/day.

The procedure as described induced a *C. difficile* infection in the test animals, from which all animals treated only with vehicle died within 3 days. In contrast, all animals treated with vancomycin or compound III survived for the duration of the entire 5-day dosing period, demonstrating the protective effects of this compound.

In a second experiment (FIG. 2), groups of 6 hamsters were first dosed with a subcutaneous dose of 10 mg/kg clindamycin phosphate, followed 24 h later with approximately $10^7$ cells of *C. difficile* strain ATCC BAA-1382. After a further 24 h, the groups were then treated either with vehicle, vancomycin or compound I three times daily at 50 mg/kg/day. The procedure described for the second experiment allows the establishment of a *C. difficile* infection from which the animal may be rescued by an effective antibiotic. As FIG. 2 demonstrates, compound I was equally effective in rescuing the animals as the currently accepted clinical standard, vancomycin.

Example 4

Activity of Type-B Lantibiotics Against Other Gut Organisms

The compounds provided herein may have improved selectivity for pathogenic bacteria compared to vancomycin. These compounds may have improved selectivity for *Clostridium difficile* over gut flora, such as *Bifidobacterium* spp and *Bacteroides* spp.

The activities of several compounds (deoxyactagardine, vancomycin and compound III) against a number of species commonly occurring as part of the gut flora were measured and compared with vancomycin (Table 5). The compounds were found to have low potency against *Bifidobacterium* spp and *Bacteroides* spp and it can therefore fairly be assumed that they would have no significant effect on the gut flora at therapeutic doses levels, unlike vancomycin.

TABLE 5

Activity of Type-B Lantibiotics Against Organisms Common in the Intestinal Flora.

| | Minimal Inhibitory Concentration (MIC) µg/ml | | |
|---|---|---|---|
| Organism | Deoxyacta-gardine B | III | Vancomycin |
| *E. coli* DC2 (membrane more susceptible) | >64 | >64 | >64 |
| *E. coli* ATCC 25922 | >64 | >64 | >64 |
| *E. faecium* (VSE) ATCC 19579 | 64 | 16 | 0.5 |
| *E. faecium* (VSE) ATCC 29212 | 8 | 4 | 4 |
| *E. coli* DC2 (membrane more susceptible) | >64 | >64 | >64 |
| *E. faecium* (VRE) (clinical isolate) | >64 | 64 | >64 |
| *E. faecium* (VRE) (clinical isolate) | 4 | 4 | >64 |
| *Bifidobacterium adolescentis* NCTC 11814 | 16 | 32 | 1 |
| *Bifidobacterium longum* NCTC 11818 | 16 | 32 | 1-2 |
| *Bacteroides fragilis* NCTC 9343 | >64 | >64 | 32 |
| *Bacteroides thetaiotaomicron* NCTC 10582 | >64 | >64 | 64 |

Example 5

Stability of Type-B Lantibiotics in Simulated Gastric and Intestinal Fluids

The lantibiotic-based compounds provided herein may have increased stability to enzymatic degradation compared to type-A lantibiotics, such as nisin. Particularly, the compounds may have improved stability to intestinal juices compared to type-A lantibiotics.

Nisin, mersacidin, compound I and compound III were tested for their susceptibility towards enzymatic digestion in the stomach. Nisin, mersacidin and compound III were tested for their susceptibility towards enzymatic digestion in the intestine. The SGF and SIF were based on the standard USP solutions for simulated gastric and simulated intestinal fluids and their activity confirmed against Bovine Serum Albumin (Hilger et al, *Clin. Exp. Immunol*. 2001, 123, 387-94). The compounds were incubated in SGF or SIF at 37° C. and their concentrations quantified by analytical HPLC (UV detection at 210 nm). The potential degradation of each compound was also monitored qualitatively by measuring in vitro antibacterial activity against *Micrococcus luteus*.

Figure 4:
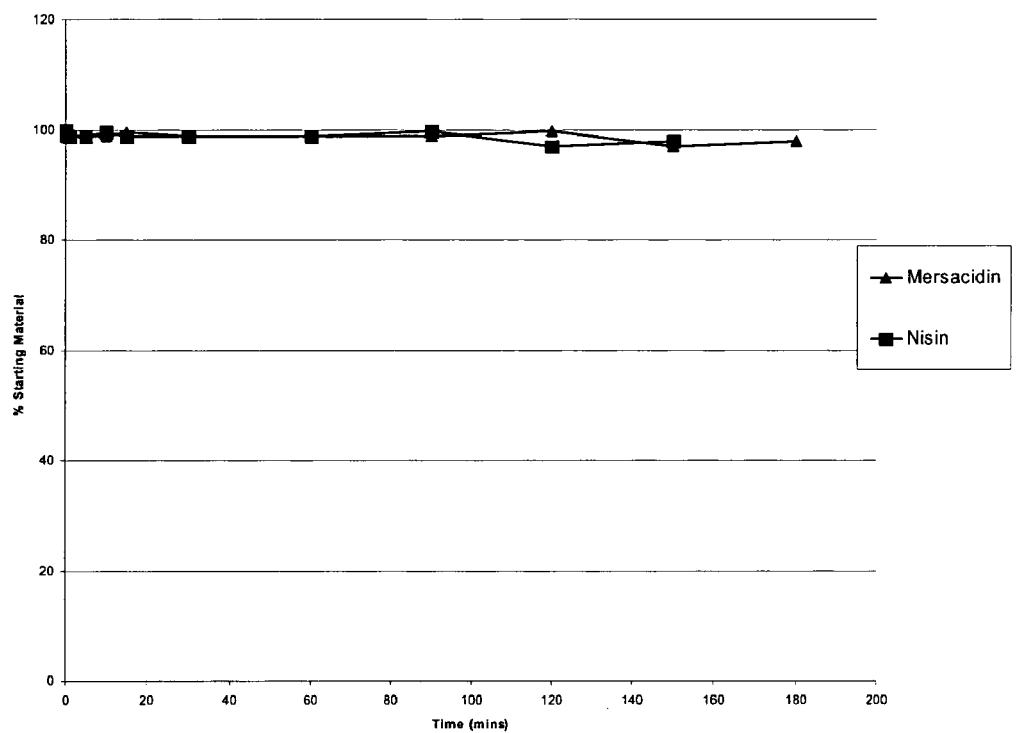
FIG. 4 shows the stability of (a) nisin and mersacidin and (b) compounds I and III in simulated gastric fluid (SGF).
Figure 4:
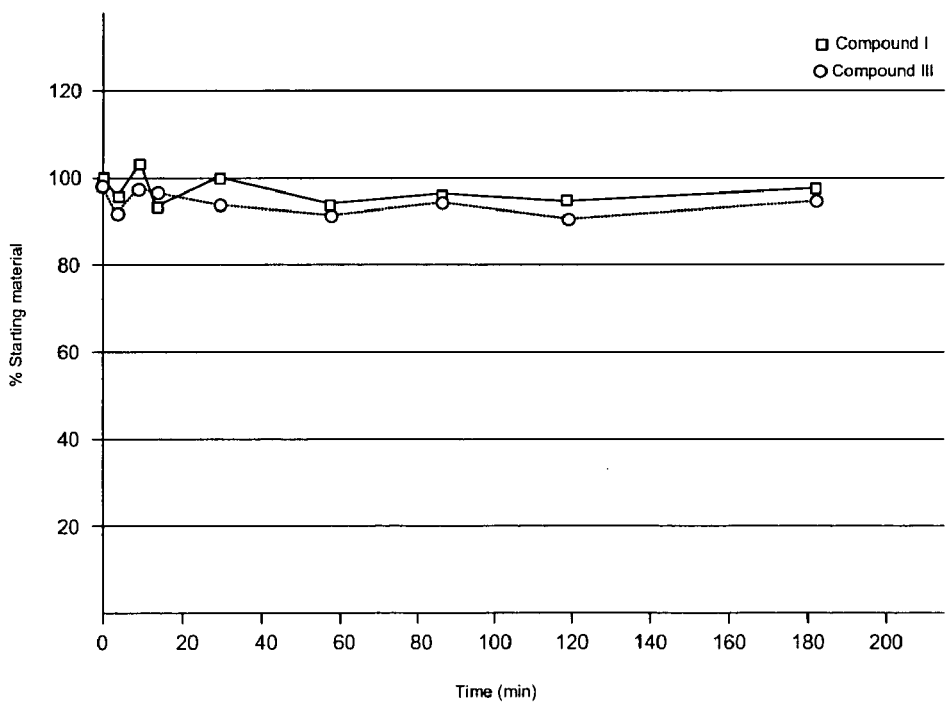

FIG. 4 shows the concentration of (a) nisin and mersacidin and (b) compounds I and III as a function of time in Simulated Gastric Fluid. The compounds tested did not show appreciable degradation in SGF.

Figure 5:
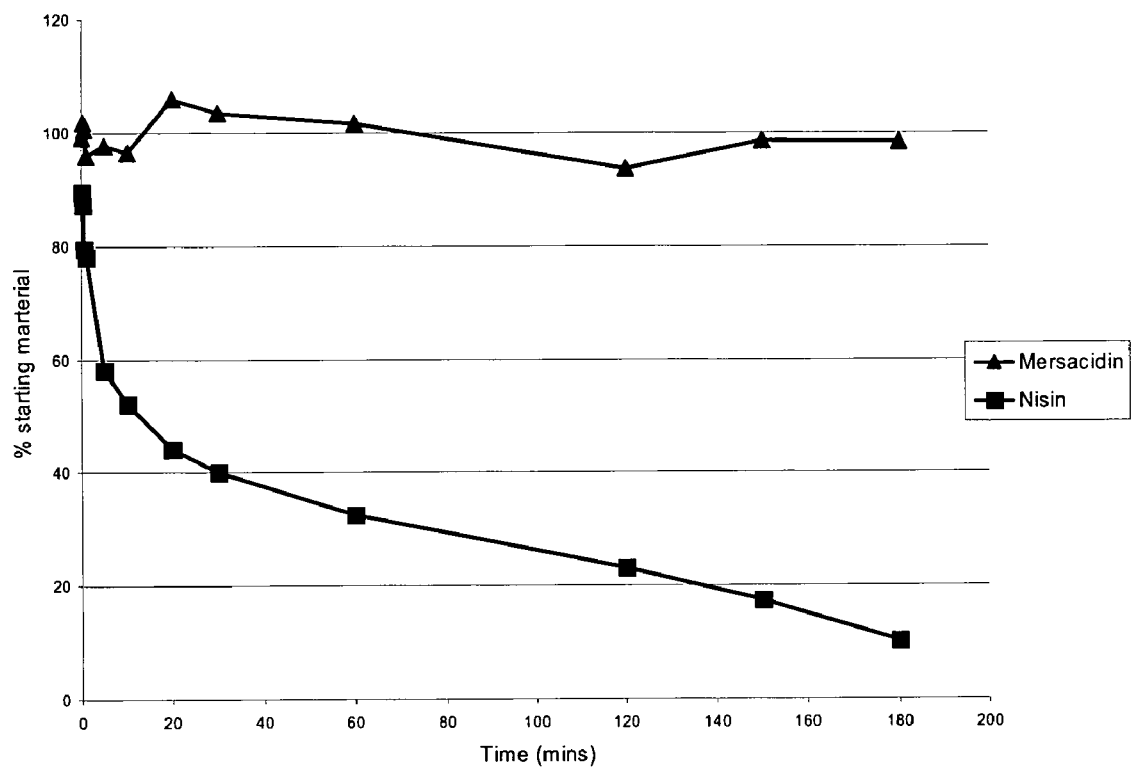
FIG. 5 shows the stability of (a) nisin and mersacidin and (b) compound III in simulated intestinal fluid (SIF).
Figure 5:
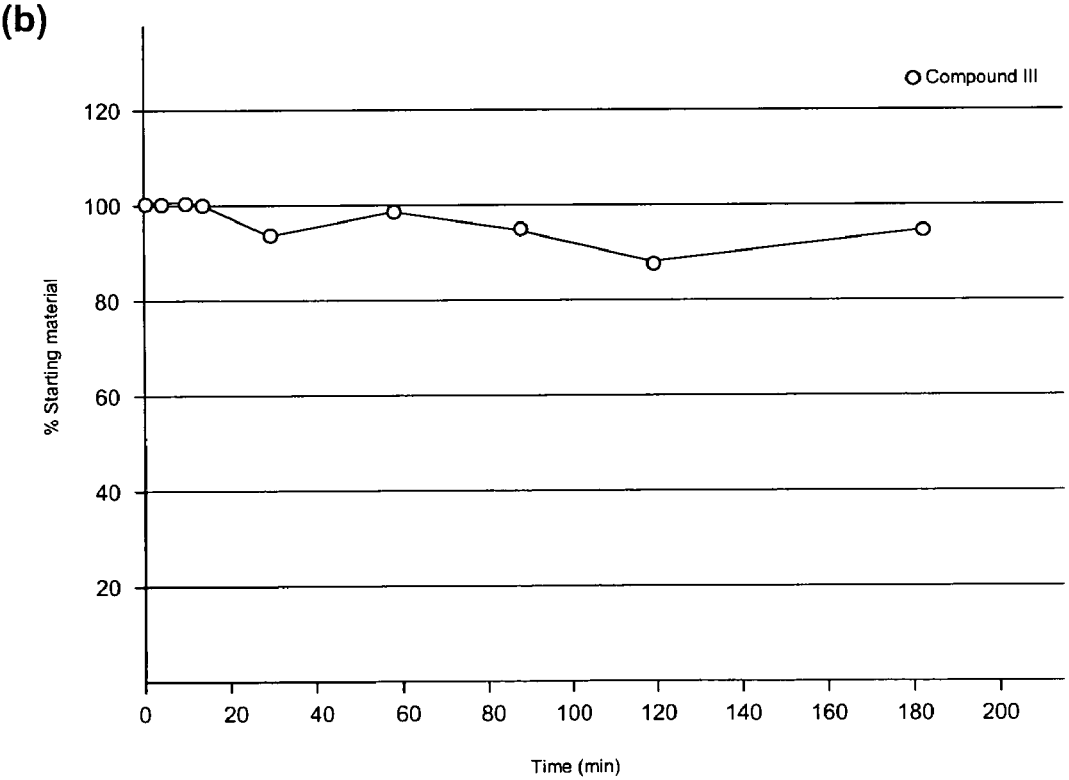

In contrast, FIG. 5 (a) shows that nisin was rapidly degraded in SIF with a half-life of approximately 15 minutes.

The rapid degradation of nisin in this medium supports the observation that the clinical utility of nisin for the treatment of colonic infections is very limited unless the compound can be protected from degradative enzymes by means of careful formulation.

FIG. 5 (b) also shows that compound III is essentially stable in SIF and that for these compounds metabolic instability is unlikely to be a factor affecting their efficacy in treating colonic C. difficile infections. The concentration data obtained by HPLC was corroborated by in vitro activity against M. luteus, which remained unaltered for mersacidin and deoxyactagardine B during the course of the experiment.

Example 6

In Vivo Stability of Type-B Antibiotics

For the purpose of treating intestinal Clostridium difficile infections with an orally administered, non-absorbed antibiotic it is of great importance that the compound is resistant to digestive enzymes and metabolism by the intestinal flora such that high concentrations can be achieved at the site of infection, typically the colon. Whilst in vitro models of gastric and intestinal fluids can provide an early indication of GI stability of a compound, in vivo experiments may provide more direct evidence that the compound reached the site of infection. In the Male Sprague-Dawley rats were dosed with compound I at 100 mg/kg via the oral route. Faeces and urine were collected over a 48 h period in two batches (at 24 h and 48 h post dose). Blood samples were taken at various time points for the first 24 h.

Analysis of the various biological samples for the parent compound showed that at least 35% of compound I was excreted in faeces unchanged, demonstrating that high colonic concentrations of the type-B antibiotic can be achieved. No material was recovered from plasma or urine after oral dosing, a result consistent with low GI absorption.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

REFERENCES

The following references are incorporated by reference herein in their entirety:

U.S. Pat. No. 6,022,851
PCT/G 82007/000138 (WO/2007/083112)
Berge, et al., J. Pharm. Sci 1997, 66, 1-19
Chatterjee, Paul, Xie and van der Donk, Chem. Rev. 2005, 105, 633
Hilger et al, Clin. Exp. Immunol. 2001, 123, 387-94
van Kraaij, de Vos, Siezen and Kuipers, Nat. Prod. Rep. 1999, 16, 575
Parenti, Pagani, Beretta, J. Antibiotics 1976, 29, 501
Sahl and Bierbaum Annual Rev. Microbiol. 1998, 52, 41-79
Zimmerman, Metzger and Jung, Eur. J. Biochem. 1995, 228, 786
Merck Novabiochem™ catalog 'Reagents for Peptide and High-Throughput Synthesis' (2006/7)
"Remington: The Science and Practice of Pharmacy", 20th Edition, 2000, pub. Lippincott, Williams & Wilkins
"Protective Groups in Organic Synthesis" (T. Green and P. Wuts; 3rd Edition; John Wiley and Sons, 1999)

The invention claimed is:

1. A compound of the formula:

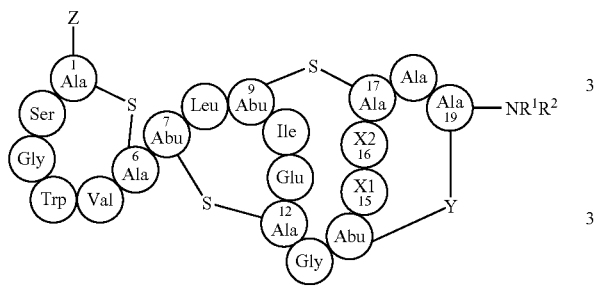

wherein:
X1-X2- represents -Leu-Val-, -Leu-Leu-, -Leu-Ile-, -Val-Leu-, Val-Ile-, -Ile-Leu-, Ile-Val- or -Ile-Ile-;

$R^1$ represents an alkyl or heteroalkyl group, substituted by at least one hydroxyl substituent, and $R^2$ represents hydrogen, or an alkyl or heteroalkyl group, optionally substituted by at least one hydroxyl substituent, or $R^1$ and $R^2$ taken together with the nitrogen atom represent a heterocyclic group having at least one hydroxyl substituent, wherein the heterocyclic group optionally further contains one or more heteroatoms;

Z is an amino acid residue, $—NR^3R^4$, $—NR^5COR^6$, $—NR^5C(O)OR^6$; $—NR^5SOR^6$, $—NR^5SO_2R^6$; $—NR^5C(S)NR^6R^7$, $—NR^5C(NR^8)NR^6R^7$, or $—N{=}R^9$, where $R^3$, $R^4$, $R^5$, $R^6$, $R^7$, $R^8$ and $R^9$ are independently hydrogen, or a group, optionally substituted, selected from alkyl, heteroalkyl, aryl, heteroaryl, aralkyl and heteroaralkyl, with the proviso that $R^9$ is not hydrogen;

Y is $—S—$ or $—S(O)—$;
or a pharmaceutically acceptable salt thereof.

2. A compound according to claim 1, wherein Z is $—NH_2$, an amino acid or $—NR^5COR^6$.

3. A compound according to claim 1 or claim 2, wherein Z is an amino acid selected from the group Ala, Ile-, Lle-, Lys-, Phe-, Val-, Glu-, Asp-, His-, Leu-, Arg-, Ser- and Trp- and said amino acids are in the D- or L-configuration.

4. A compound according to claim 2, wherein Z is $—NR^5COR^6$ and $R^5$ is hydrogen.

5. A compound according to claim 1, wherein $R^2$ is hydrogen.

6. A compound according to claim 1, wherein -X1-X2- represents -Leu-Val- or -Val-Ile-.

7. A compound according to claim 1, wherein $R^1$ is a $C_{1-7}$ alkyl group substituted by at least one hydroxyl substituent.

8. A compound according to claim 1, wherein $R^1$ has one, two or three hydroxyl group substituents.

9. A compound according to claim 1, wherein $R^1$ is selected from the group consisting of:

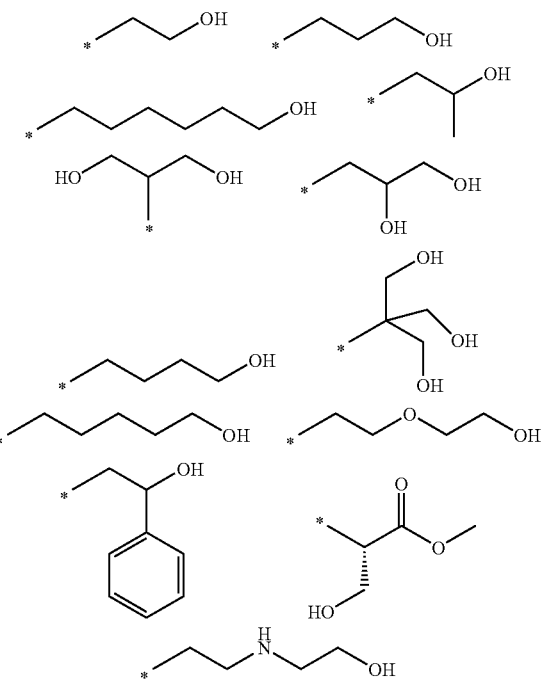

wherein * indicates the point of attachment to the nitrogen atom.

10. A compound according to claim 1, wherein $R^1$ is $—CH_2CH_2OH$.

11. A compound according to claim 1, wherein $R^1$ is selected from the group consisting of:

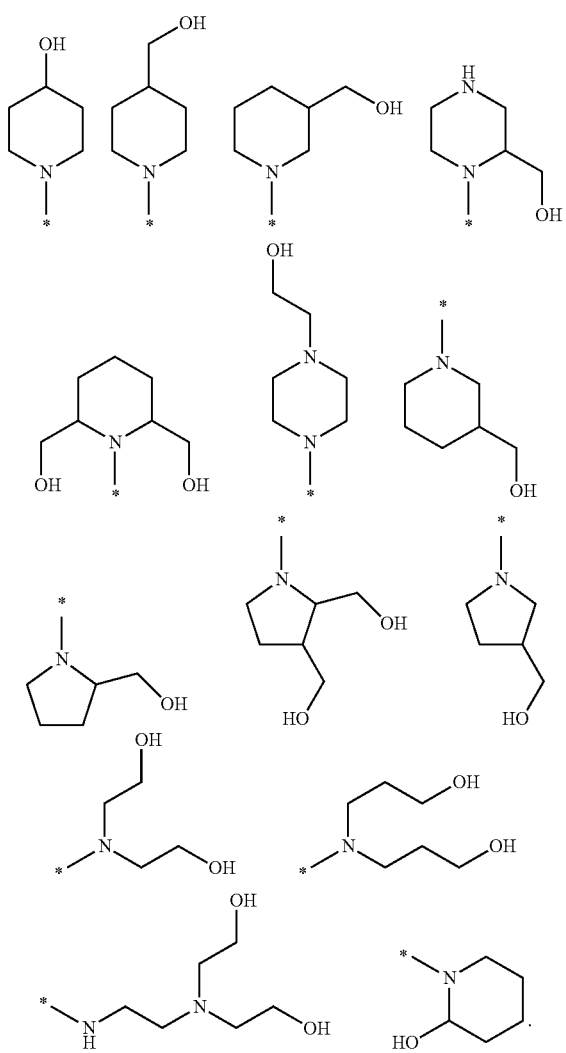

12. A compound according to claim 1, wherein the compound is selected from the group consisting of:
Compound I: Deoxy-Actagardine B N-[2-ethanolamine] monocarboxamide;
Compound II: Deoxy-Actagardine B N-[4-butanolamine] monocarboxamide;
Compound III: Actagardine N-[2-ethanolamine]monocarboxamide;
Compound IV: Deoxy-actagardine B (3-amino-1,2-propanediol) monocarboxamide;
Compound V: Deoxy-actagardine B (2-amino-1,3-propanol) monocarboxamide;
Compound VI: Deoxy-actagardine B [tris(hydroxymethyl)methylamine]monocarboxamide;
Compound VII: Deoxy-actagardine B (1-amino-2-propanol) monocarboxamide;
Compound VIII: Deoxy-actagardine B (1-amino-3-propanol) monocarboxamide;
Compound IX: (L)-Phenylalanyl-(O)-deoxyactagardine B (ethanolamine) monocarboxamide;
Compound X: (L)-Tryptophanyl-(O)-deoxyactagardine B (ethanolamine) monocarboxamide;
Compound XI: (L)-Alanyl-(O)-deoxyactagardine B (ethanolamine) monocarboxamide;
Compound XII: (D)-Alanyl-(O)-deoxyactagardine B (ethanolamine) monocarboxamide;
Compound XIII: (L)-Isoleucinyl-(O)-deoxyactagardine B (ethanolamine) monocarboxamide;
Compound XIV: (L)-Leucinyl-(O)-deoxyactagardine B (ethanolamine) monocarboxamide;
Compound XV: N-Phenylacetyl deoxyactagardine B (ethanolamine) monocarboxamide;
Compound XVI: N-Acetyl deoxyactagardine B (ethanolamine) monocarboxamide;
Compound XVII: N-Mandelyl deoxyactagardine B (ethanolamine) monocarboxamide;
Compound XVIII: Deoxyactagardine B (N,N-bis(2-hydroxyethyl)ethylene diamine) monocarboxamide;
Compound XX: Deoxy-Actagardine B N-[2-hydroxy-2-phenylethylamine] monocarboxamide;
Compound XXI: Deoxy-actagardine B (L-serine methyl ester) monocarboxamide;
Compound XXII: Deoxyactagardine B (N-(2-hydroxyethyl)ethylenediamine) monocarboxamide;
Compound XXIII: Deoxy-actagardine B (2-hydroxypiperazine) monocarboxamide;
Compound XXX: (L)-Alanyl-(0)-deoxyactagardine B (ethanolamine) monocarboxamide;
Compound XXXI: (D)-Alanyl-(0)-deoxyactagardine B (ethanolamine) monocarboxamide;
Compound XXXII: (L)-Isoleucinyl-(0)-deoxyactagardine B (ethanolamine) monocarboxamide;
Compound XXXIII: (L)-Leucinyl-(0)-deoxyactagardine B (ethanolamine) monocarboxamide;
Compound XXXIV: N-Phenylacetyl deoxyactagardine B (ethanolamine) monocarboxamide;
Compound XXXV: N-Acetyl deoxyactagardine B (ethanolamine) monocarboxamide; and
Compound XXXVI: N-Mandelyl deoxyactagardine B (ethanolamine) monocarboxamide.

13. A variant of a compound as described in claim 1, wherein the 1, 2, 3 or 4 amino acids are at positions selected from positions 2, 3, 4, 5, 8, 10, 11, 13, 15, 16 or 18 of the compound.

14. A pharmaceutical composition comprising a compound according to claim 1 and a pharmaceutically acceptable carrier or diluent.

15. A method for the treatment of a bacterial infection in a subject, the method comprising administering to said subject an effective amount of a compound according to claim 1.

16. The method of claim 15, wherein the bacterial infection is an *Enterococcus* sp, *Streptococcus* spp, *Staphylococcus* spp, or *Clostridium difficile* infection.

17. The method of claim 16, wherein the bacterial infection is a *Clostridium difficile* infection.

18. A pharmaceutical composition comprising a variant according to claim 13 and a pharmaceutically acceptable carrier or diluent.

19. A method for the treatment of a bacterial infection in a subject, the method comprising administering to said subject an effective amount of a variant according to claim 13.

20. A method for the treatment of a bacterial infection in a subject, the method comprising administering to said subject an effective amount of a pharmaceutical composition according to claim 14.

* * * * *

SEQUENCE LISTING

<160> NUMBER OF SEQ ID NOS: 22

<210> SEQ ID NO 1
<211> LENGTH: 19
<212> TYPE: PRT
<213> ORGANISM: Actinoplanes garbadinensis

<400> SEQUENCE: 1

Ser Ser Gly Trp Val Cys Thr Leu Thr Ile Glu Cys Gly Thr Val Ile
1               5                   10                  15

Cys Ala Cys

<210> SEQ ID NO 2
<211> LENGTH: 19
<212> TYPE: PRT
<213> ORGANISM: Actinoplanes liguriae

<400> SEQUENCE: 2

Ser Ser Gly Trp Val Cys Thr Leu Thr Ile Glu Cys Gly Thr Leu Val
1               5                   10                  15

Cys Ala Cys

<210> SEQ ID NO 3
<211> LENGTH: 19
<212> TYPE: PRT
<213> ORGANISM: Artificial sequence
<220> FEATURE:
<223> OTHER INFORMATION: Synthetic sequence: Compound of Formula I of

```
                       PCT/GB2008/002465
<220> FEATURE:
<221> NAME/KEY: THI

```
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 5

Ala Ser Gly Trp Val Ala Xaa Leu Xaa Ile Glu Ala Gly Xaa Leu Ile
1               5                   10                  15

Ala Ala Ala

<210> SEQ ID NO 6
<211> LENGTH: 19
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 6

Ala Ser Gly Trp Val Ala Xaa Leu Xaa Ile Glu Ala Gly Xaa Val Leu
1               5                   10                  15

Ala Ala Ala

<210> SEQ ID NO 7
<211> LENGTH: 19
```

```
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 7

Ala Ser Gly Trp Val Ala Xaa Leu Xaa Ile Glu Ala Gly Xaa Val Val
1               5                   10                  15

Ala Ala Ala

<210> SEQ ID NO 8
<211> LENGTH: 19
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 8

Ala Ser Gly Trp Val Ala Xaa Leu Xaa Ile Glu Ala Gly Xaa Val Ile
1               5                   10                  15

Ala Ala Ala
```

```
<210> SEQ ID NO 9
<211> LENGTH: 19
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 9

Ala Ser Gly Trp Val Ala Xaa Leu Xaa Ile Glu Ala Gly Xaa Ile Leu
1               5                   10                  15

Ala Ala Ala

<210> SEQ ID NO 10
<211> LENGTH: 19
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 10

Ala Ser Gly Trp Val Ala Xaa Leu Xaa Ile Glu Ala Gly Xaa Ile Val
1               5                   10                  15

Ala Ala Ala
```

```
<210> SEQ ID NO 11
<211> LENGTH: 19
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: THIOETH
<222> LOCATION: (1)..(6)
<220> FEATURE:
<221> NAME/KEY: MISC_FEATURE
<222> LOCATION: (7)..(7)
<223> OTHER INFORMATION: Xaa can represent Thr or 4Abu
<220> FEATURE:
<221> NAME/KEY: MISC_FEATURE
<222> LOCATION: (9)..(9)
<223> OTHER INFORMATION: Xaa can represent Thr or 4Abu
<220> FEATURE:
<221> NAME/KEY: MISC_FEATURE
<222> LOCATION: (14)..(14)
<223> OTHER INFORMATION: Xaa can represent Thr or 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: MISC_FEATURE
<222> LOCATION: (14)..(19)
<223> OTHER INFORMATION: Linked by Y, where Y is -S- or -S(O)-

<400> SEQUENCE: 11

Ala Ser Gly Trp Val Ala Xaa Leu Xaa Ile Glu Ala Gly Xaa Ile Ile
1               5                   10                  15

Ala Ala Ala

<210> SEQ ID NO 12
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
```

-continued

```
<221> NAME/KEY: MISC_FEATURE
<222> LOCATION: (15)..(20)
<223> OTHER INFORMATION: Linked by Y, where Y is -S- or -S(O)-

<400> SEQUENCE: 12

Xaa Ala Ser Gly Trp Val Ala Xaa Leu Xaa Ile Glu Ala Gly Xaa Leu
1               5                   10                  15

Leu Ala Ala Ala
            20

<210> SEQ ID NO 13
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 13

Xaa Ala Ser Gly Trp Val Ala Xaa Leu Xaa Ile Glu Ala Gly Xaa Leu
1               5                   10                  15

Val Ala Ala Ala
            20

<210> SEQ ID NO 14
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
```

```
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 14

Xaa Ala Ser Gly Trp Val Ala Xaa Leu Xaa Ile Glu Ala Gly Xaa Leu
1               5                   10                  15

Ile Ala Ala Ala
            20

<210> SEQ ID NO 15
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 15

Xaa Ala Ser Gly Trp Val Ala Xaa Leu Xaa Ile Glu Ala Gly Xaa Val
1               5                   10                  15

Leu Ala Ala Ala
```

```
<210> SEQ ID NO 16
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 16

Xaa Ala Ser Gly Trp Val Ala Xaa Leu Xaa Ile Glu Ala Gly Xaa Val
1               5                   10                  15

Val Ala Ala Ala
            20

<210> SEQ ID NO 17
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
```

```
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 17

Xaa Ala Ser Gly Trp Val Ala Xaa Leu Xaa Ile Glu Ala Gly Xaa Val
1               5                   10                  15

Ile Ala Ala Ala
            20

<210> SEQ ID NO 18
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 18

Xaa Ala Ser Gly Trp Val Ala Xaa Leu Xaa Ile Glu Ala Gly Xaa Ile
1               5                   10                  15

Leu Ala Ala Ala
            20

<210> SEQ ID NO 19
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
```

```
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by Y, where Y is -S- or -S(O)-

<400> SEQUENCE: 19

Xaa Ala Ser Gly Trp Val Ala Xaa Leu Xaa Ile Glu Ala Gly Xaa Ile
1               5                   10                  15

Val Ala Ala Ala
            20

<210> SEQ ID NO 20
<211> LENGTH: 20
<212> TYPE: PRT
<213> ORGANISM: Artificial sequence
<220> FEATURE:
<223> OTHER INFORMATION: Synthetic sequence: Compound of Formula I of
      PCT/GB2008/002465
<220> FEATURE:
<221> NAME/KEY: VARIANT
<222> LOCATION: (1)..(1)
<223> OTHER INFORMATION: Xaa can be any naturally occurring amino acid
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
```

```
<221> NAME/KEY: MISC_FEATURE
<222> LOCATION: (15)..(20)
<223> OTHER INFORMATION: Linked by Y, where Y is -S- or -S(O)-

<400> SEQUENCE: 20

Xaa Ala Ser Gly Trp Val Ala Xaa Leu Xaa Ile Glu Ala Gly Xaa Ile
1               5                   10                  15

Ile Ala Ala Ala
            20

<210> SEQ ID NO 21
<211> LENGTH: 20
<212> TYPE: PRT
<213> ORGANISM: Artificial sequence
<220> FEATURE:
<223> OTHER INFORMATION: Synthetic sequence: Compound IX of
      PCT/GB2008/002465
<220> FEATURE:
<221> NAME/KEY: SITE
<222> LOCATION: (1)..(2)
<223> OTHER INFORMATION: Phe is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by -S-

<400> SEQUENCE: 21

Phe Ala Ser Gly Trp Val Ala Xaa Leu Xaa Ile Glu Ala Gly Xaa Leu
1               5                   10                  15

Val Ala Ala Ala
            20

<210> SEQ ID NO 22
<211> LENGTH: 20
<212> TYPE: PRT
<213> ORGANISM: Artificial sequence
<220> FEATURE:
<223> OTHER INFORMATION: Synthetic sequence: Compound X of
      PCT/GB2008/002465
<220> FEATURE:
<221> NAME/KEY: SITE
<222> LOCATION: (1)..(2)
<223> OTHER INFORMATION: Tyr is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MISC_FEATURE
<222> LOCATION: (8)..(8)
<223> OTHER INFORMATION: Xaa can represent Thr or 4Abu
```

```
<220> FEATURE:
<221> NAME/KEY: MISC_FEATURE
<222> LOCATION: (10)..(10)
<223> OTHER INFORMATION: Xaa can represent Thr or 4Abu
<220> FEATURE:
<221> NAME/KEY: MISC_FEATURE
<222> LOCATION: (15)..(15)
<223> OTHER INFORMATION: Xaa can represent Thr or 4Abu
<220> FEATURE:
<221> NAME/KEY: THIOETH
<222> LOCATION: (10)..(18)
<220> FEATURE:
<221> NAME/KEY: MISC_FEATURE
<222> LOCATION: (15)..(20)
<223> OTHER INFORMATION: Linked by -S-

<400> SEQUENCE: 22

Tyr Ala Ser Gly Trp Val Ala Xaa Leu Xaa Ile Glu Ala Gly Xaa Leu
1               5                   10                  15

Val Ala Ala Ala
            20
```